United States Patent [19]
Liu et al.

[11] Patent Number: 6,025,159
[45] Date of Patent: Feb. 15, 2000

[54] **D-AMINO ACID OXIDASE PROMOTER FROM *T. VARIABILIS***

[75] Inventors: Suo W. Liu, Manlius; Thomas Franceschini, East Syracuse, both of N.Y.

[73] Assignee: Bristol-Myers Squibb Company, New York, N.Y.

[21] Appl. No.: 09/099,564

[22] Filed: Jun. 18, 1998

Related U.S. Application Data

[60] Provisional application No. 60/050,740, Jun. 25, 1997.
[51] Int. Cl.$^7$ ..................................... C12P 21/02
[52] U.S. Cl. .................... 435/69.1; 435/252.33; 435/254.21; 435/320.1; 536/24.1
[58] Field of Search .................. 435/320.1, 252.33, 435/254.21; 536/69.1, 24.1

[56] References Cited

U.S. PATENT DOCUMENTS 5,453,374  9/1995  Furuya et al. ..................... 435/254.11

OTHER PUBLICATIONS

Maxam et al. (1977), Proc. Natl. Acad. Sci USA, vol. 74, No. 2, pp. 560–564.

Sanger et al. (1977), Proc. Natl. Acad. Sci, USA, vol. 74, No. 12, pp. 5463–5467.

*Primary Examiner*—James Ketter
*Attorney, Agent, or Firm*—Thomas R. Savitsky; Christopher A. Klein; Audrey F. Sher

[57] ABSTRACT

A D-amino acid oxidase promoter isolated from *T. variabilis* has been incorporated into *S. cerevisiae* expression vectors to increase the expression of heterologous genes. The heterologous promoter has been placed upstream of selective markers, auxotrophic nutritional and/or dominant selectable markers. Because the promoter is from another yeast specie, it is weakly recognized by and *S. cerevisiae*. To compensate for the weak transcripts of selectable marker genes transcribed from the weak heterologous promoter, the plasmid containing the gene of the interest is amplified leading to a higher expression of protein of interest.

34 Claims, 17 Drawing Sheets

1 2 3

1 2

D-AMINO ACID OXIDASE PROMOTER FROM *T. VARIABILIS*

This application claims the benefit of U.S. Provisional Application No. 60/050,740, filed Jun. 25, 1997.

FIELD OF THE INVENTION

The present invention concerns a novel promoter from the D-amino acid oxidase gene from *Trigonopsis variabilis*.

BACKGROUND OF THE INVENTION

Various molecular techniques have been utilized to increase expression of heterologous genes in various host systems such as *E. coli, Saccharomyces cerevisiae*, and other expression systems. Among the techniques used to increase the heterologous protein expression level is to increase the transcriptional rate, to increase the translational rate, and to decrease the degradation rate of the expressed proteins. Due to several desirable features, *S. cerevisiae* has been used as a host to express various proteins of interest. For example, heterologous proteins in *S. cerevisiae* are generally soluble. *S. cerevisiae* does perform glycosylation. Furthermore, there are well-established processes for large-scale production of yeast and yeast products. However, in general, the expression level in *S. cerevisiae* is low.

In general, *S. cerevisiae* has two types of expression plasmids, an autonomous replicating plasmid and an integrating plasmid. An autonomous replicating plasmid typically has the following salient features:

(1) A 2 µcircle DNA fragment for the autonomous maintenance of the plasmid.

(2) A yeast selectable marker which can be nutritional and complements the host nutritional deficiency such as ura3, leu, his or dominant selectable markers such as the neomycin phosphotransferase gene. The expression of the neomycin phosphotransferase gene allows it to survive in the presence of the drug Geneticin™. The promoter for the selectable marker genes is generally the native promoter of the gene itself (i.e., ura3, leu, his) or a promoter from another *S. cerevisiae* strain.

(3) A strong *S. cerevisiae* promoter followed by multiple cloning sites for the insertion of genes of interest.

(4) Procaryotic sequences such as an ampicillin resistance gene and colE1 origin of replication to permit growth and maintenance in *E. coli*.

The integration vector typically has the following salient features:

(1) A yeast selection marker which can be nutritional which complements the host's defect or one of the dominant selectable markers.

(2) A strong *S. cerevisiae* promoter followed by multiple cloning sites for the insertion of genes of interest.

(3) Procaryotic sequences such as an ampicillin resistance gene and colE1 origin of replication to permit growth and maintenance in *E. coli*.

We have discovered that replacement of the promoter to the selectable marker with the weak promoter from the D-amino acid oxidase promoter from *T. variabilis* leads to the amplification of the plasmid containing the gene of interest.

SUMMARY OF THE INVENTION

The present invention is directed to isolated nucleic acid comprising a promoter region of the D-amino acid oxidase gene isolated from *T. variabilis*. The sequence of the promoter has been determined and is SEQ. ID. NO.:1. The invention also concerns expression vectors containing the promoter of the invention, particularly those vectors useful for expression in *S. cerevisiae*. Preferred expression vectors of the invention have the novel promoter placed upstream of a *S. cerevisiae* selectable marker. This manipulation of the vector leads to an increase of the expression of the desired protein cloned in the same vector containing the promoter.

Figure 17:
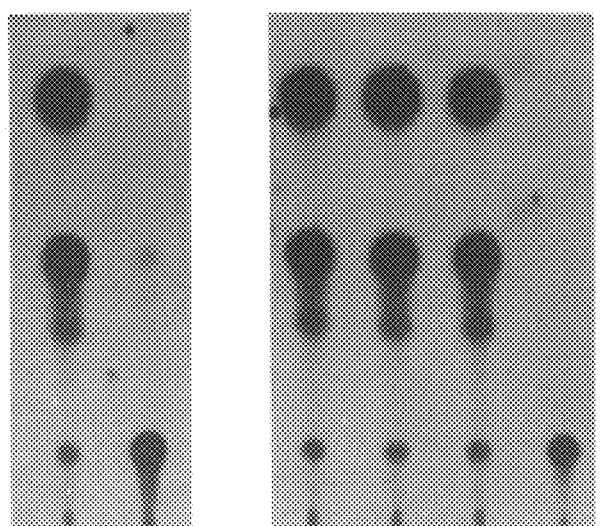

Lane 1: pYBM31DAAO (−control)
Lane 2: pYBM31pDAAOBCAT #3
Lane 3: pYBM31pDAAOBCAT #11
Lane 4: *E. coli* pBM 11CAT (+control)
Lane 5: [$^{14}$C]Chloramphenicol FIG. 17 Plasmid pYBM31pDAAOECAT was transfected into DBY745. The transformants obtained were grown overnight with aeration at 30° C. in SD medium supplemented with 2% glucose, leucine and adenine. The cells were harvested by centrifugation, resuspended in water and lysed by supernatant the cells in the presence of glass beads. The debris were removed by centrifugation and the supernatant assayed for CAT activity.

Figure 18:
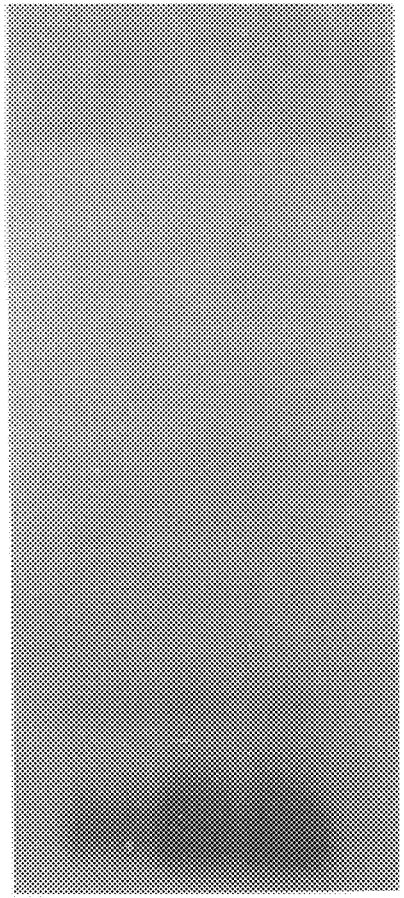

Lane 1: *E. coli* CAT (+control)
Lane 2: pYBM31pDAAOEco
Lane 3: pYBM31pDAAOB
Lane 4: pYBM31PDAAOECAT
Lane 5: pYBM31pDAAOHCAT
Lane 6: [$^{14}$C]Chloramphenicol FIG. 18 Amplification of pYBMURA3B/b/a.

The β-lactamase gene was cloned into the unique NcoI-BamHI site of both pYBM31TPImc and pYBMura3B in order to direct the expression of β-lactamase from the TPI promoter. The recombinant plasmid was transformed into *S. cerevisiae* strain DBY746 . Transformants were selected on minimal media plates without uracil and cultured in selective medium.

Figure 19:
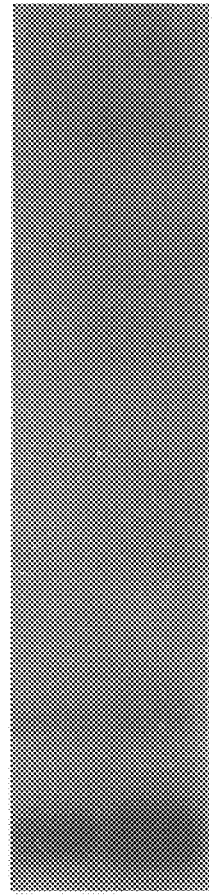

Total DNA was isolated from the transformants, digested with HindIII, electrophoresed in 0.7% agarose for Southern transfer, and hybridized to $^{32}$P labeled β-lactamase DNA.

lane 1:100 ng of total DBY746 DNA transformed with pYBM31TPImc1/bla lane 2: 100 ng of total DBY746 DNA transformed with pYBMura3B/bla, transformants A lane 3:100 ng of total DBY746 DNA transformed with pYBMura3B/bla, transformant B FIG. 19 Amplification of pYBMURA3B/TGF-α.

The human TGF gene was cloned into the unique NcoI-BamHI site of both pYBM31TPImc and pYBMura3B in order to direct the expression of TGF-α from the TPI promoter. The recombinant plasmid was transformed into S. cerevisiae strain DBY746. Transformants were selected on minimal media plates without uracil and cultured in selective medium.

Total DNA was isolated from the transformants, digested with HindIII, electrophoresed in 0.7% agarose for Southern transfer, and hybridized to $^{32}P$ labeled human TGF-α DNA.

lane 1: 100 ng of total DBY746 DNA transformed with pYBM31TPImc/TGF-α.

lane 2: 100 ng of total DBY746 DNA transformed with pYBMura3D/TGF-α.

DETAILED DESCRIPTION OF THE INVENTION

To increase the level of the expression in S. cerevisiae, we have increased the DNA level by replacing the promoter of selectable markers with the promoter of D-amino acid oxidase isolated from T. variabilis. Because the promoter from T. variabilis is weakly recognized by the transcriptional elements from S. cerevisiae, the plasmid containing the selectable marker containing the T. variabilis promoter is amplified to allow the host to survive in the presence of the selective pressure. The increase in the copy number of the expression plasmids leads to an increased level of the expression of the protein of interest.

The selectable marker useful in the expression vector of the invention can be any selectable marker known in the art, for example, nutritional auxotrophic markers such as ura3, leu, his, dominant selectable markers such as the gene coding for resistance to Geneticin™, and the like.

The promoter of the D-amino acid oxidase gene from T. variabilis has been cloned and its sequence has been determined and is SEQ. ID. NO.:1.

The genes to be expressed by the expression vectors of the invention can be any gene coding for a protein or peptide of interest.

All DNA sequences are represented herein by formulas whose left to right orientation is in the conventional direction of 5' to 3'. Nucleotide base abbreviations used herein are conventional in the art, i.e., T is thymine, A is adenine, C is cytosine, and G is guanine. The present invention includes the promoter having the DNA sequence of SEQ.ID.NO.:1; or a DNA sequence complementary thereto; or a DNA sequence which hybridizes to a DNA sequence complementary thereto. Preferably, the DNA sequence hybridizes under stringent conditions. Stringent hybridization conditions select for DNA sequences of greater than 80% homology, preferably greater than 85% or, more preferably, greater than 90% homology. Screening DNA under stringent conditions may be carried out according to the method described in Nature, 313: 402–404 (1985). The DNA sequences capable of hybridizing under stringent conditions with the DNA disclosed in the present application may be, for example, modified sequences, allelic variants of the disclosed DNA sequences, may be naturally present in T. variabilis but related to the disclosed DNA sequence, or may be derived from other fungal sources. An exact sequence may be shorter or longer the the sequence of SEQ.ID.NO.:1, but as long as it hybridizes to SEQ.ID.NO.:1 under stringent conditions, such sequence is within the scope of the present invention. General techniques of nucleic acid hybridization are disclosed by Maniatis, T. et al., In: *Molecular Cloning, a Laboratory Manual*, Cold Spring Harbor, N.Y. (19820, and by Haymes, B. D. et al., In: *Nucleic Acid Hybridization, a Practical Approach*, IRL Press, Washington, D.C. (1985), which references are incorporated herein by reference.

It is also contemplated that the present invention encompasses modified sequences. As used in the present application, the term "modified", when referring to a nucleotide sequence, means a nucleotide sequence which differs from the wild-type sequence found in nature.

The DNA sequences of the present invention can be obtained using various methods well-known to those of ordinary skill in the art. The promoter and expression vectors can be partly or wholly synthesized chemically and/or partly or wholly prepared through genetic engineering techniques. Fragments can be sequentially ligated (via appropriate terminal restriction sites or complementary terminal sequences) so as to form the correct linear sequence of nucleotides.

The promoter DNA sequence of the present invention can also be modified (i.e., mutated) to prepare various mutations. These mutations may permit higher levels of production of the expressed peptide, easier purification of the peptide, or provide additional restriction endonuclease recognition sites. All such modified DNA and polypeptide molecules are included within the scope of the present invention.

The expression vectors of the invention comprise the novel promoter and, optionally, one or more other regulatory DNA sequences operatively linked to the DNA sequence coding for all or part of the peptide desired to be expressed. As used in this context, the term "operatively linked" means that the regulatory DNA sequences are capable of directing the replication and/or the expression of the DNA sequence coding for all or part of the desired protein or peptide.

Expression vectors of the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto. The expression vectors of the invention are preferable plasmids. It is preferred that the plasmids of the invention are constructed such that the promoter of the invention has been placed upstream of one or more selectable markers. Replacement of a S. cerevisiae promoter located upstream to a selectable marker with the weakly recognized heterologous promoter of the invention leads to gene amplification of the desired gene cloned in the expression vector containing the novel promoter.

Expression vectors useful in the present invention typically contain an origin of replication, the promoter of the invention located in front (i.e., upstream of) the DNA sequence coding for the selectable marker and for the protein or peptide desired to be expressed. The protein or peptide desired to be expressed can be, for example, D-amino acid oxidase, chloramphenicol acetyl transferase, TGF-α, β-lactamase, microbial esterases such as *Rhodosporidium esterase*, monoclonal antibodies, insulin, interferon, epidermal growth factor, growth hormone, and the like. The DNA sequence coding for all or part of the structural protein (i.e., polypeptide desired to be expressed) is followed by transcription termination sequences and the remaining vector. The expression vectors may also include other DNA sequences known the art, for example, stability leader sequences which provide for stability of the expression product, secretory leader sequences which provide for secretion of the expression product, sequences which allow expression of the structural gene to modulated (e.g., by the presence or absence of nutrients or other inducers in the growth medium), marking sequences which are capable of providing phenotypic selection in transformed host cells, stability elements such as centromeres which provide mitotic stability to the plasmid, and sequences which provide sites for cleavage by restriction endonucleases. The characteristics of the actual expression vector used must be compatible with the host cell which is to be employed. Certain expression vectors may contain a fungal autonomously replicating sequence (ARS; e.g., ARS from *Fusarium oxysporum* and *Saccharomyces cerevisiae*) which promotes in vivo production of self-replicating plasmids in fungal hosts. It is preferred that the fungal expression vectors of the invention have a fungal ARS sequence and thus will not integrate into host chromosomes upon plasmid entry of host cells. An expression vector as contemplated by the present invention is at least capable of directing the replication in fungal cells, and preferably *S. cerevisiae*. Suitable origins of replication in *S. cerevisiae* include the replication determinant of the yeast 2 μmicron circle plasmid. Suitable termination sequences include, for example, the trpC terminator from *A. nidulans*, yeast alcohol dehydrogenase (ADH), and the like. It is also preferred that the expression vector include a sequence coding for a selectable marker. As mentioned hereinbefore, the selectable marker can be selectable marker known as the art such as ura3, leu, his, Geneticin™ resistance, phleomycin resistance, and the like. The selectable marker is preferably ura3. All of these materials are known in the art and are commercially available.

Suitable expression vectors containing the desired coding and control sequences may be constructed using standard recombinant DNA techniques known in the art, many of which are described in Sambrook et al. Molecular Cloning: A Laboratory Manual, 2nd edition, Cold Spring Harbor Laboratory, Cold Spring Harbor, N.Y. (1989).

The present invention additionally concerns host cells containing an expression vectors of the invention. The host cells preferably contain an expression vector substantially as shown in FIGS. 1–15. Suitable host cells include fungal cells, for example, *S. cerevisiae, R. toruloides, Cephalosporium acremonium*, and *Penicillium chrysogenum* cells, preferred is *S. cerevisiae*. Especially preferred is the strain *Saccharomyces cerevisiae* ATCC 44773 containing plasmid pYBMura3B. Another preferred organism is *Saccharomyces cerevisiae* ATCC 44774 containing the plasmid pYBMura3Bsuc2. The term "ATCC" as used herein refers to the accession number of the American Type Culture Collection, 12301 Parklawn Drive, Rockville, Md. 20852, the depository for the organism referred to. *Escherichia coli* ATCC 98469 containing plasmid pYBMura3B was deposited with the ATCC on Jun. 18, 1997, under the provisions of the Budapest Treaty and *Escherichia coli* ATCC 98470 containing control plasmid pYM31TPImc was deposited with the ATCC on Jun. 18, 1997, under the provisions of the Budapest Treaty.

Expression vectors may be introduced into host cells by various methods known in the art. For example, transfection of host cells with expression vectors can be carried out by the polyethylene glycol mediated protoplast transformation method. However, other methods for introducing expression vectors into host cells, for example, electroporation, biolistic injection, or protoplast fusion, can also be employed.

Once an expression vector has been introduced into an appropriate host cell, the host cell may be cultured under conditions permitting expression of large amounts of the desired polypeptide.

In the preferred approach, the recombinant expression vector host system can be identified and selected based upon the presence or absence of certain marker gene functions. A marker gene can be placed in the same plasmid under the regulation of the same promoter. Expression of the marker gene in response to induction or selection indicates the presence of the entire recombinant expression vector.

The DNA sequences of expression vectors, plasmids or DNA molecules of the present invention may be determined by various methods known in the art. For example, the dideoxy chain termination method as described in Sanger et al., Proc. Natl. Acad. Sci. U.S.A. 74, 5463–5467 (1977), or the Maxam-Gilbert method as described in Proc. Natl. Acad. Sci. U.S.A. 74, 560–564 (1977) may be employed.

It should, of course, be understood that not all expression vectors and DNA regulatory sequences will function equally well to express DNA sequences. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns a method for producing a desired polypeptide comprising culturing a host cell containing an expression vector of the invention.

Growth of the host cells may be achieved by one of ordinary skill in the art by the use of an appropriate medium. Appropriate media for growing host cells include those which provide nutrients necessary for the growth of the cells. A typical medium for growth includes necessary carbon sources, nitrogen sources, and trace elements. Inducers may also be added. The term "inducer", as used herein, includes any compound enhancing formation of the desired protein or peptide.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium gutamate and the like; and alcohols such as ethanol, propanol and the like.

Nitrogen sources may include N-Z amine A, corn steep liquor, soy bean meal, beef extracts, yeast extracts, molasses, baker's yeast, tryptone, nutrisoy, peptone, yeastamin, sodium nitrate, ammonium sulfate and the like.

Trace elements may include phosphates and magnesium, manganese, calcium, cobalt, nickel, iron, sodium and potassium salts.

The medium employed may include more than one carbon or nitrogen source or other nutrient.

Exemplary media include aqueous media containing the following (in weight %):

| Medium 1 | |
|---|---|
| Malt Extract | 1% |
| Yeast Extract | 1% |
| Peptone | 1% |
| Glucose | 2% |
| | pH 7.0 |
| Medium 2 | |
| Peptone | 0.3% |
| Glycerol | 4% |
| Malt Extract | 1% |
| Yeast Extract | 1% |
| | pH 7.0 |

The pH of the medium is preferably adjusted to about 6 to 8, most preferably 6.5, sterilized, e.g., at a temperature of 121° C. for 30 minutes, and then adjusted to a pH of about 6.5 to 7.5, preferably 7.0, preferably 7.0, after sterilization.

The process of the present invention is performed under conditions suitable for forming the desired peptide. The pH of the medium is preferably maintained between 4.0 and 9.0, most preferably between 6.0 and 8.0, during the growth of host cells.

A suitable temperature range for the process of the invention is from about 15° C. to about 60° C. A preferred temperature range is from about 25° to about 40° C.

Pressure is not known to be critical to practice of the invention and for convenience about atmospheric pressure is typically employed.

The process of the invention is preferably carried out under aerobic conditions. The agitation and aeration of the reaction mixture affects the amount of oxygen available during the stereoselective reduction process which may be conducted, for example, in shake-flask cultures or fermentor tanks during growth of microorganisms in a single-stage or two-stage process. The agitation range from 50 to 100 RPM is preferable, with 50 to 500 RPM being most preferred. Aeration of about 0.1 to 10 volumes of air per volume of media per minute (i.e., 0.1 to 10 v/vt) is preferred, with aeration of about 5 volumes of air per volume of media per minute (i.e., 5 v/vt) being most preferred.

Adequate production of the desired peptide may take, for example, from about 4 to 48 hours, preferably 12 to 24 hours, measured from the time of initially contacting the host cells with a suitable medium.

The following examples are further illustrative of the present invention. These examples are not intended to limit the scope of the present invention, and provide further understanding of the invention.

EXAMPLES

Figure 16:
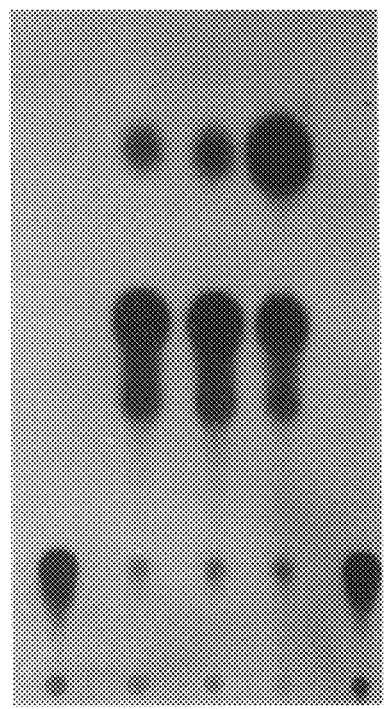
FIG. 16 Plasmid pYBM31pDAAOBCAT was transfected into DBY745. The transformants obtained were grown overnight with aeration at 30° C. in SD medium supplemented with 2% glucose, leucine and adenine. The cells were harvested by centrifugation, resuspended in water and lysed by vortexing the cells in the presence of glass beads. The debris were removed by centrifugation and the supernatant assayed for CAT activity.

In the following examples, some reagents, plasmids, restriction enzymes and other materials were obtained from commercial sources and used according to the indication by suppliers. Operations employed for the purification and characterization and the cloning of DNA and the like are well known in the art or can be adapted from the literature. To determine whether *S. cerevisiae* transcriptional elements can recognize the promoter sequence from *Trigonopsis variabilis*, the promoter of the *Trigonopsis variabilis* D-amino acid oxidase was cloned in a *S. cerevisiae* vector. The gene coding for chloramphenicol acetyltransferase (CAT) was cloned downstream from the D-amino acid oxidase. FIG. 16 indicates that the promoter sequence from *Trigonopsis variabilis* is recognized by the *S. cerevisiae* transcriptional elements. This is indicated by the conversion of the [$^{14}$C]chloramphenicol to its various acetylation derivatives: the monoacetate and the di-acetate forms. The cloning of the bacterial gene CAT cloned under the direction of the *Trigonopsis variabilis* can lead to the expression of biologically active CAT protein. As there is no indication to the length of the D-amino acid oxidase promoter from *Trigonopsis variabilis* needed to support transcription of a gene, a 1.6 kilobase (Kb) promoter element was cloned upstream of the reporter CAT gene initially. This promoter sequence was reduced in size to approximately 380 bp (EcoRI fragment) and to approximately 173 base pairs (bp) (HindIII fragment). In both cases, the promoter was able to support the transcription of the CAT gene as indicated by FIG. 17.

It has been shown herein that a heterologous promoter, specifically, the promoter of D-amino acid oxidase from *Trigonopsis variabilis*, can be recognized by the transcriptional elements from *S. cerevisiae*. The heterologous promoter is weaker than the native promoter. Replacement of the native promoter of the selectable marker of the *S. cerevisiae* with the promoter of the gene product(s) due to the amplification of the plasmid itself to compensate for the weakened promoter in the presence of the selective pressure. Three heterologous genes have been cloned in various *S. cerevisiae* vectors containing the D-amino acid oxidase promoter from *Trigonopsis variabilis*. The native promoter to the nutritional marker, ura 3, was removed and replaced with the D-amino acid oxidase promoter from *Trigonopsis variabilis* (FIG. 18). The expression of these heterologous genes was evaluated in *S. cerevisiae*. The genes are the chloramphenicol acetyltransferase (CAT), the β-lactamase gene, and the human TGF-α. In all three cases, amplifications of the gene products are observed. Table 2 shows the increased expression of the β-lactamase by approximately three fold when plasmid pYBMURA3B containing the β-lactamase gene was introduced into *S. cerevisiae*. Likewise, table 3 shows the increase in the expression of human TGF-α by approximately 2-fold upon the introduction of plasmid pYBMURA3B containing the TGF-α gene into *S. cerevisiae*. The increase in the protein expression is correlated with an increase in the plasmid copy number as determined by Southern hybridization (FIG. 18 and FIG. 19). The above expression plasmid was also used to express the esterase from Rhodosporidium, a highly glycosylated protein. (Table 4).

The utility of the expression plasmid described above is not limited to the expression of intracellular protein. The addition of a secretion signal to the above plasmid has enabled the expressed heterologous proteins, such as the human TGF-α (Table 3). A 10-Fold increase in the expressing of TGFα is observed upon the introduction of plasma pYBMura3BSuc2 containing TGF-α is introduced into *S. cerevisiae*. FIG. 18 indicates that the increase in the expression of the secreted gene product is correlated with an increase in the gene copy number of the plasmid.

Example 1

Materials and Methods

Microbial Strains and Plasmids

The plasmids, bacterial, and yeast strains used are listed in Table 1.

TABLE 1

Figure 1:
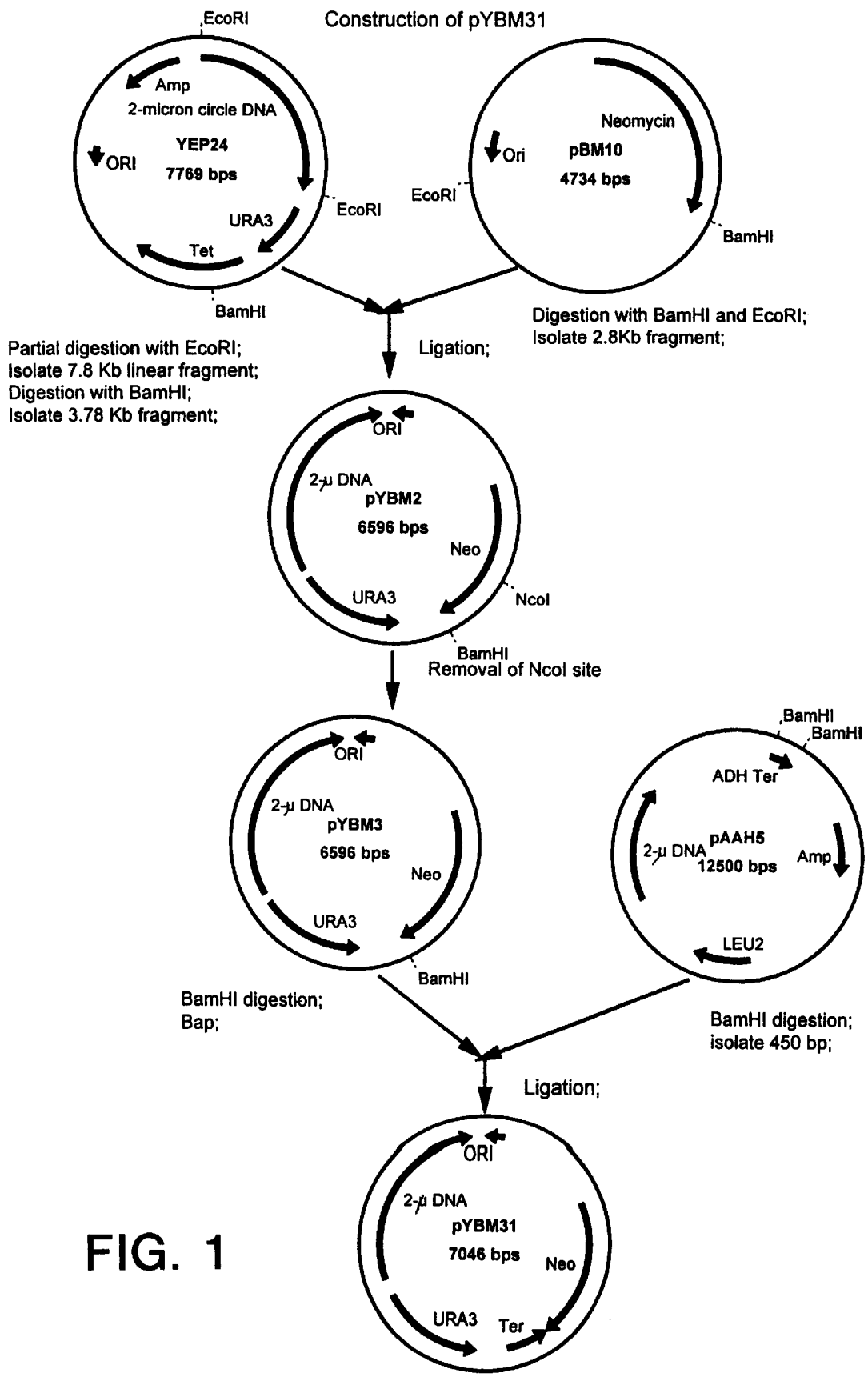
FIG. 1 Construction of pYBM31
Figure 2:
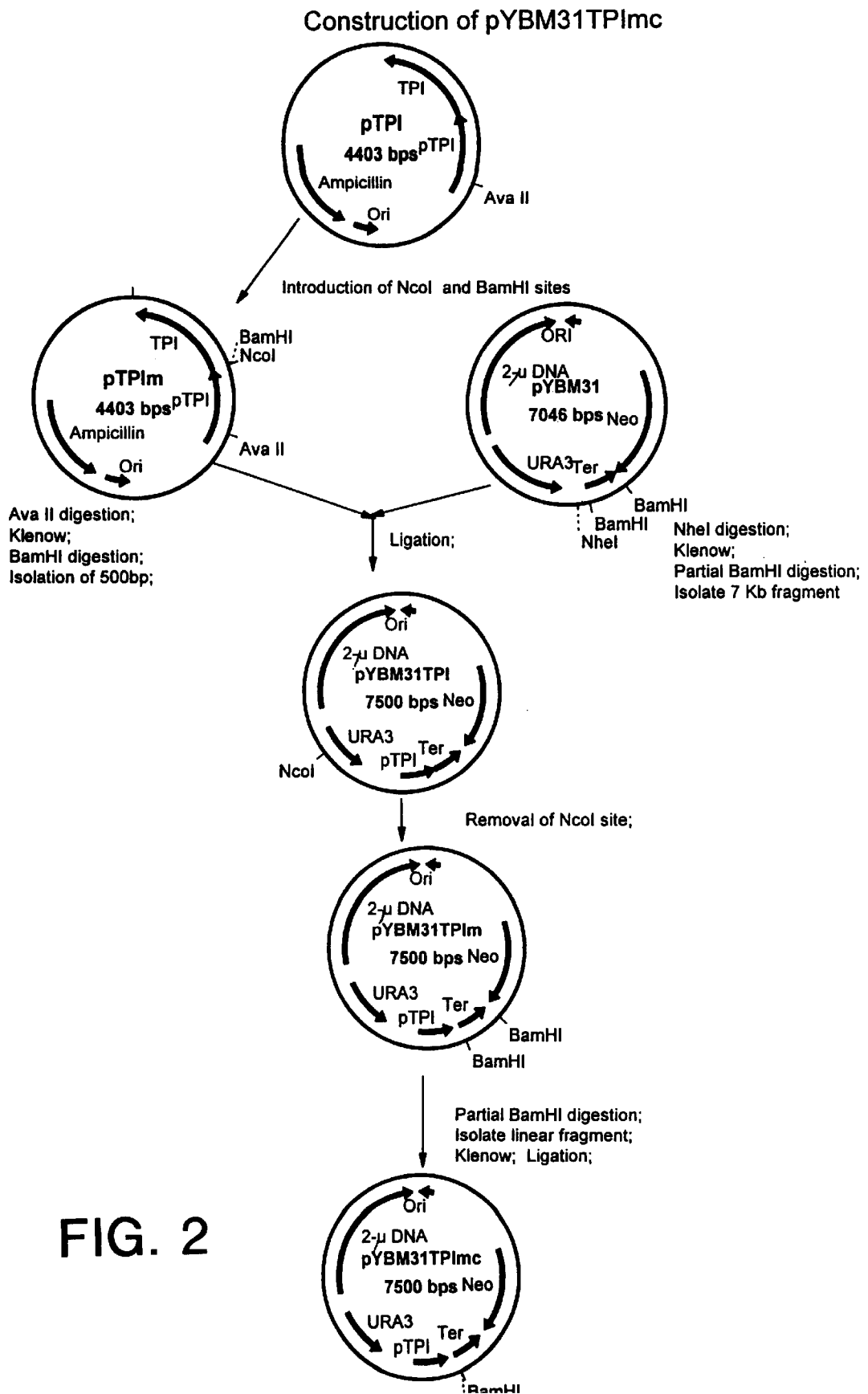
FIG. 2 Construction of pYBM31TPImc
Figure 3:
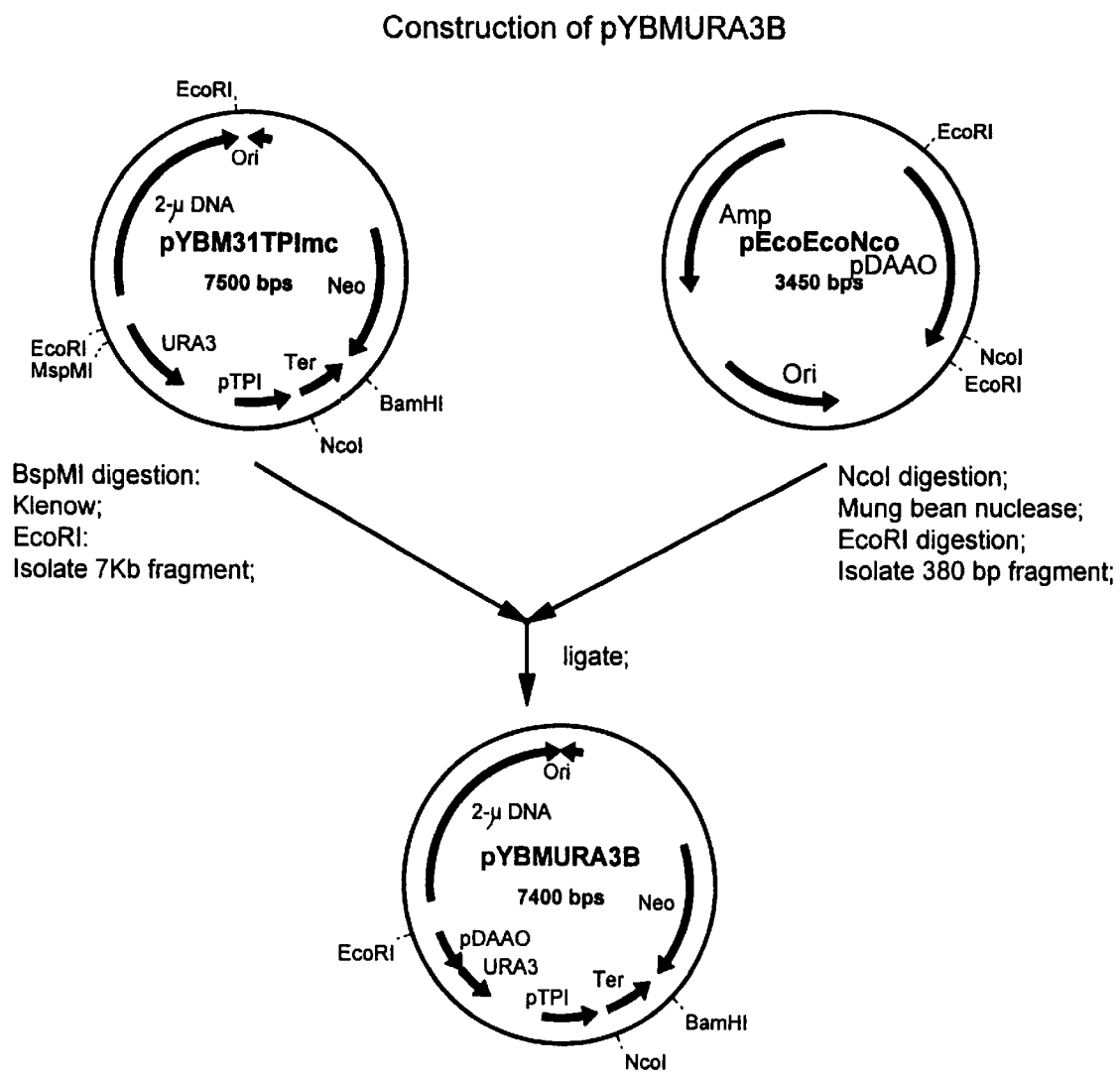
FIG. 3 Construction of pYBMURA3B
Figure 4:
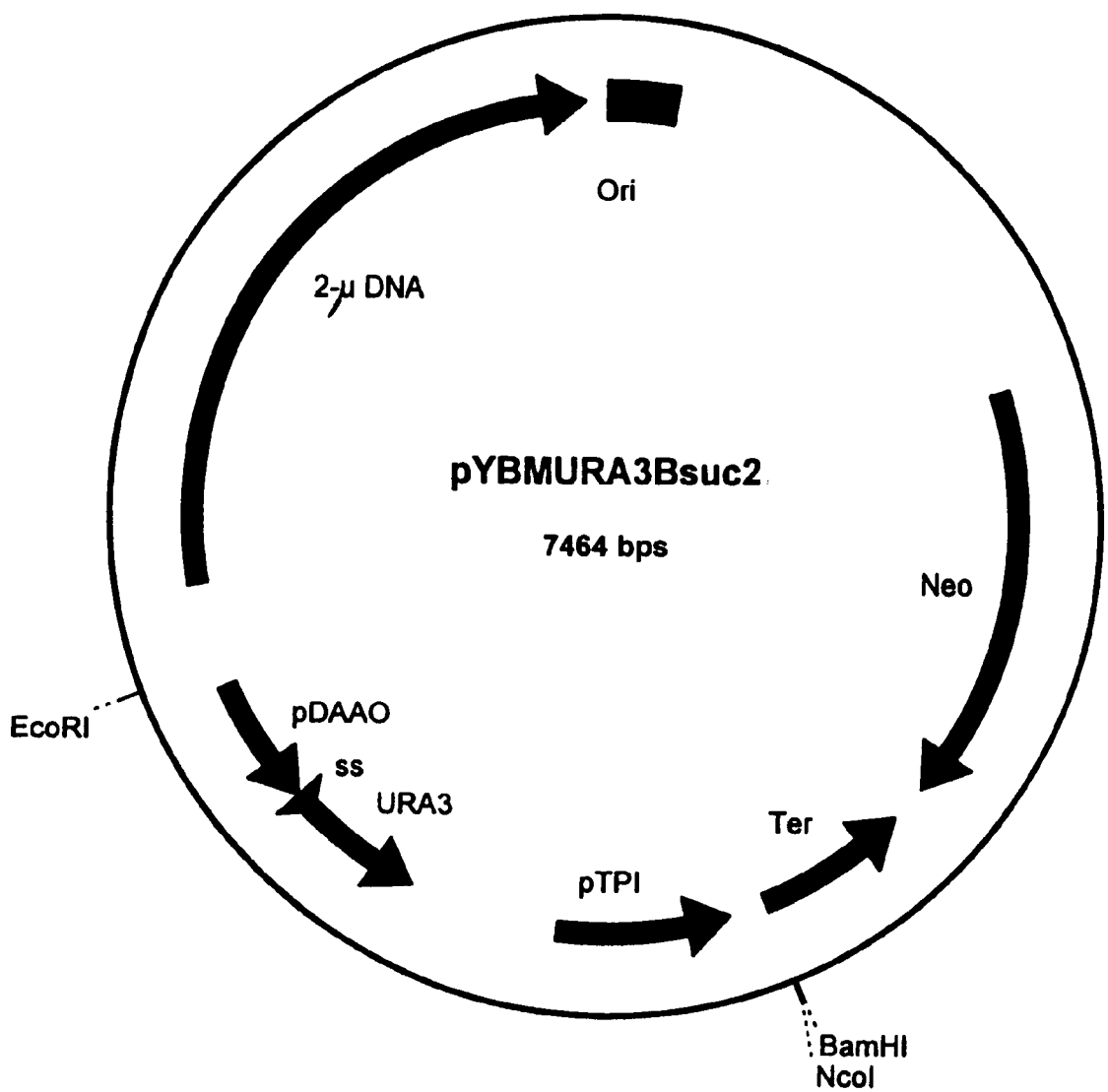
FIG. 4 pYBMURA3Bsuc2
Figure 5:
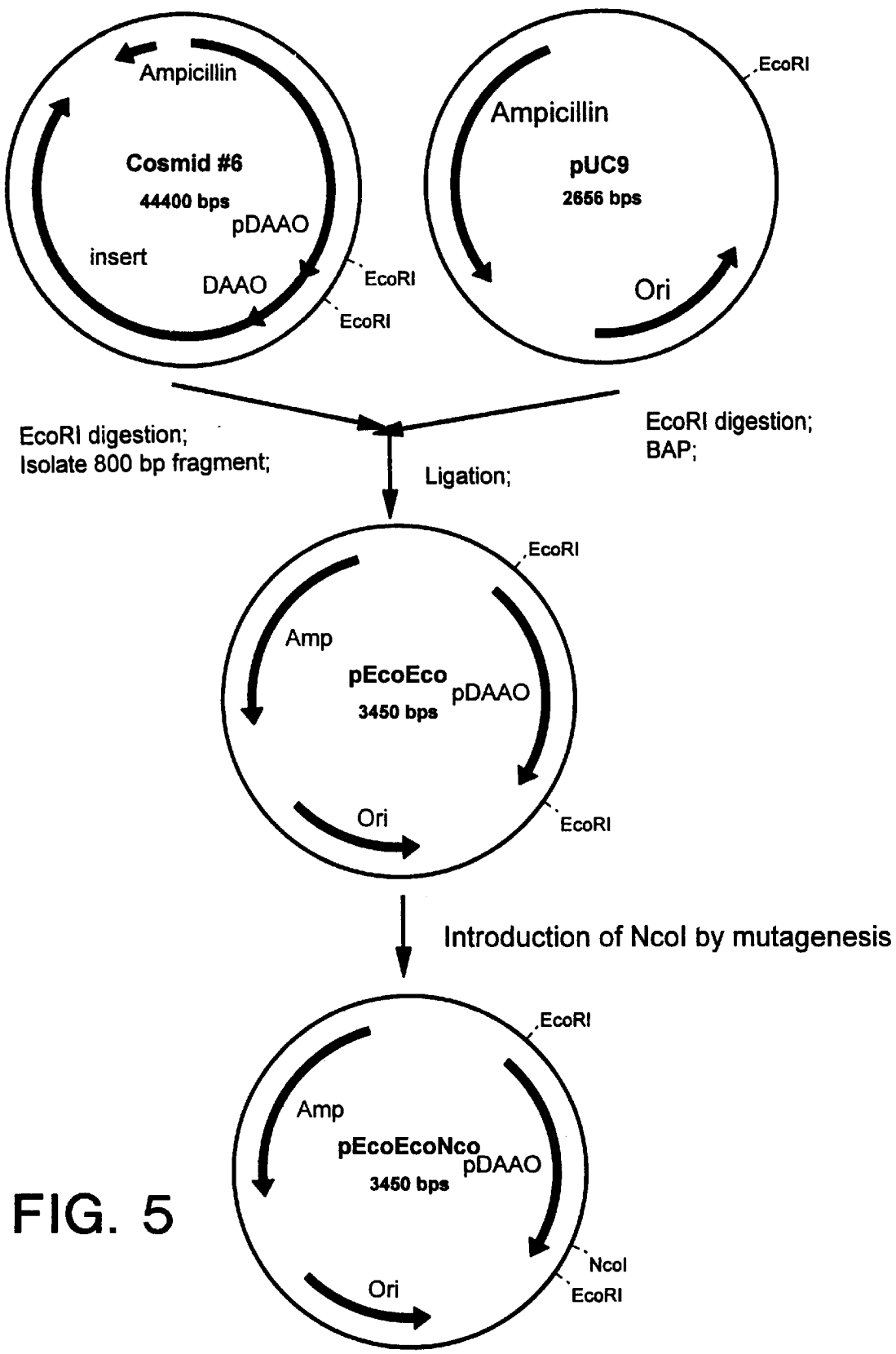
FIG. 5 Construction of pEcoEcoNco
Figure 6:
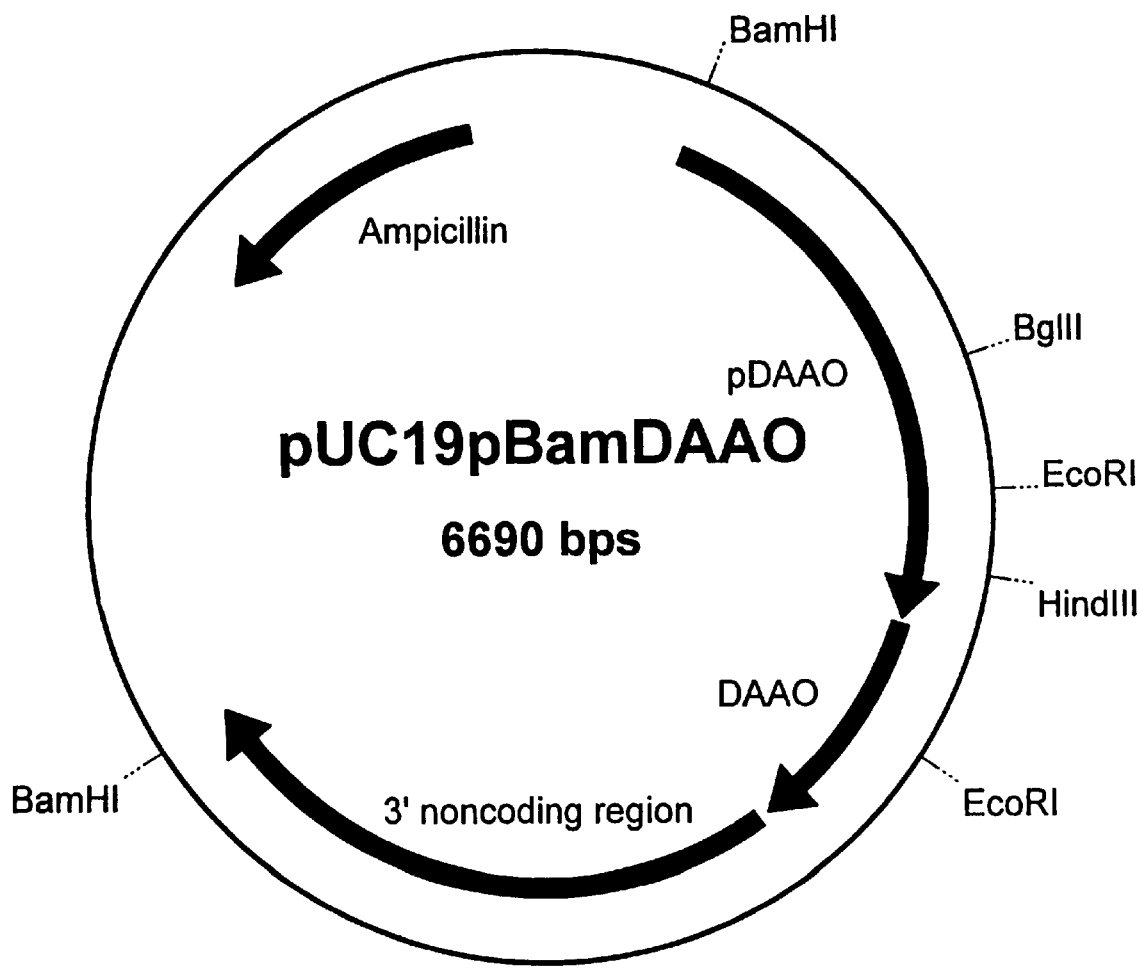
FIG. 6 pUC19pBamDAAO
Figure 7:
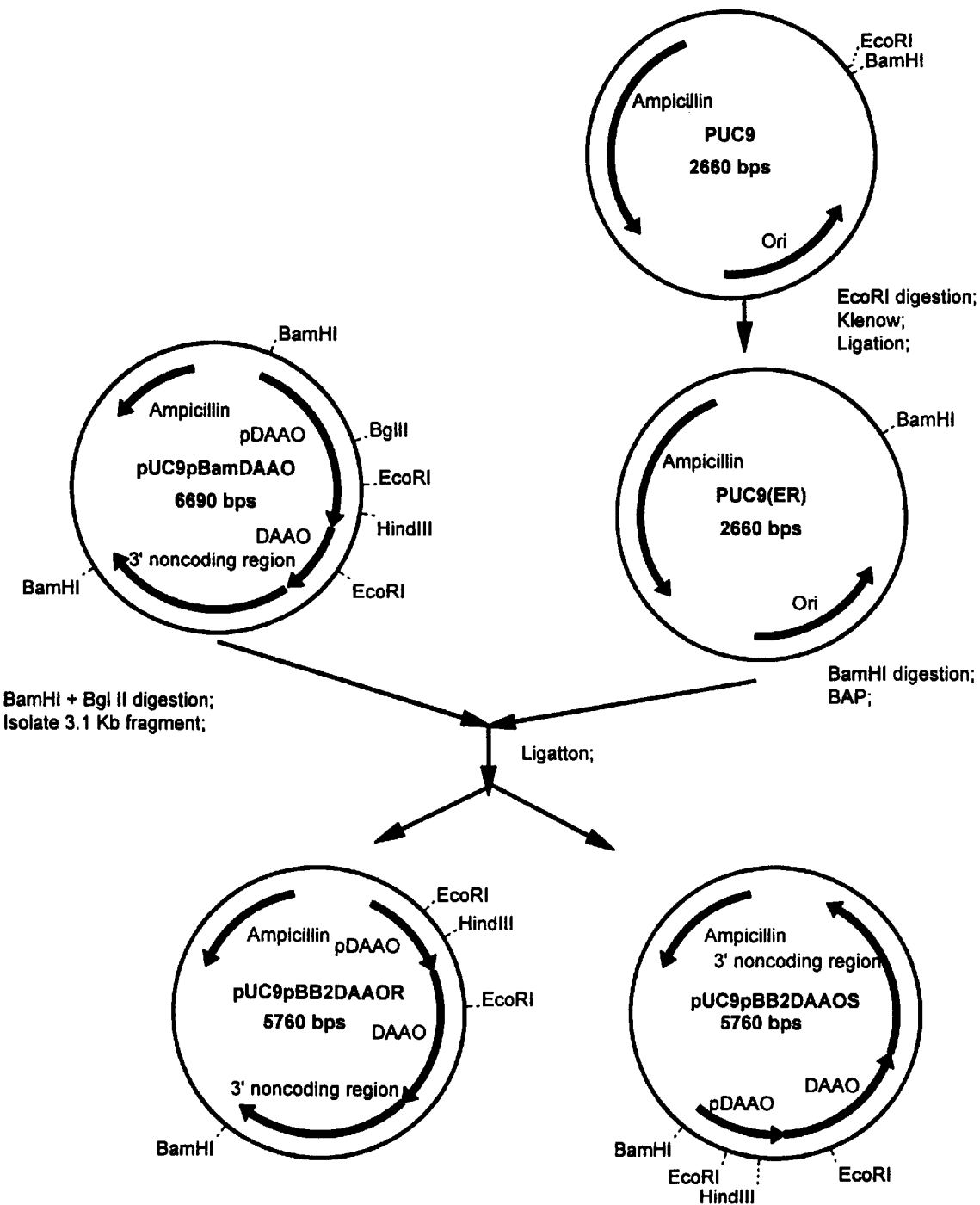
FIG. 7 Construction of pUC9BB2DAAO
Figure 8:
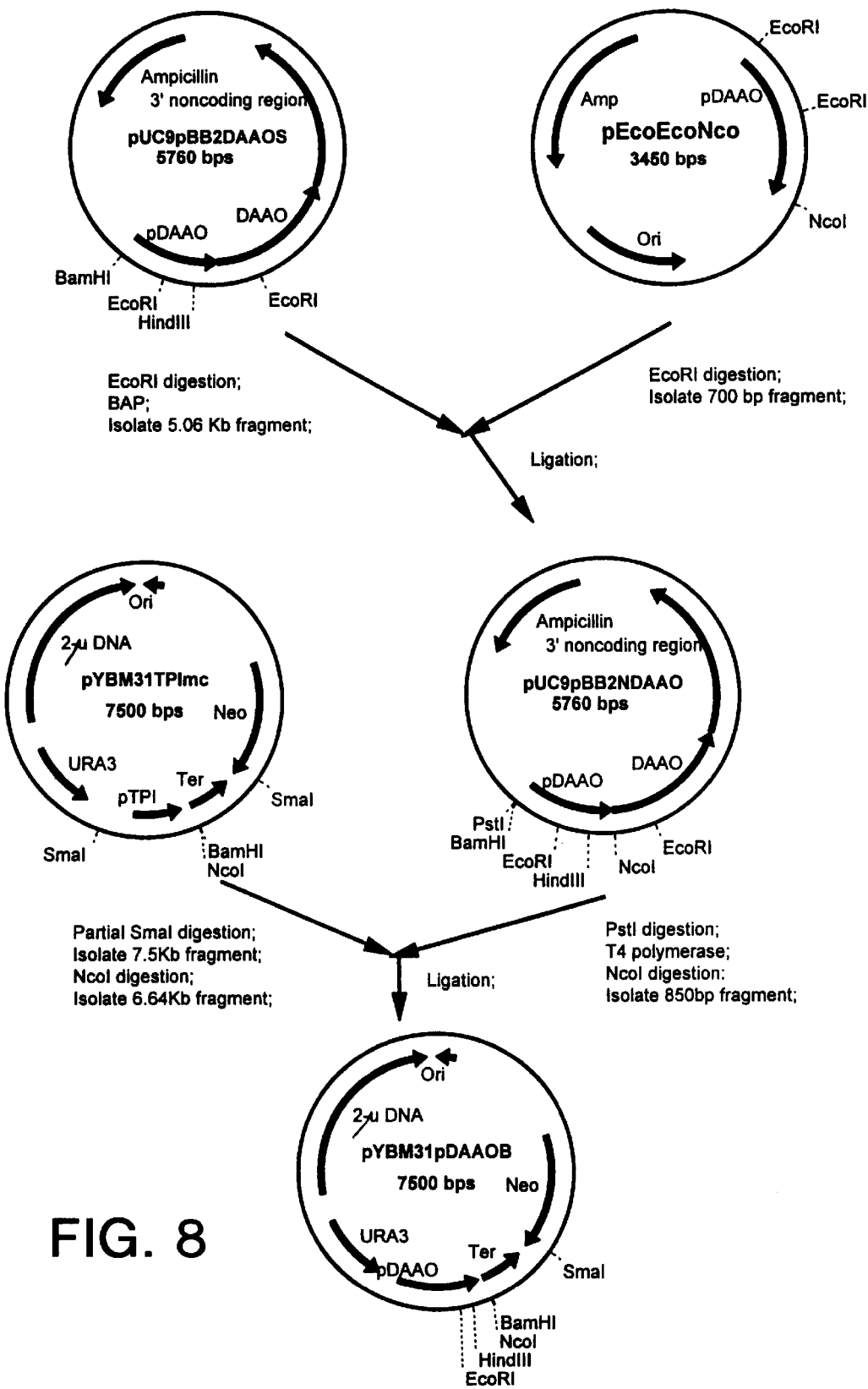
FIG. 8 Construction of pYBM31pDAAOB
Figure 9:
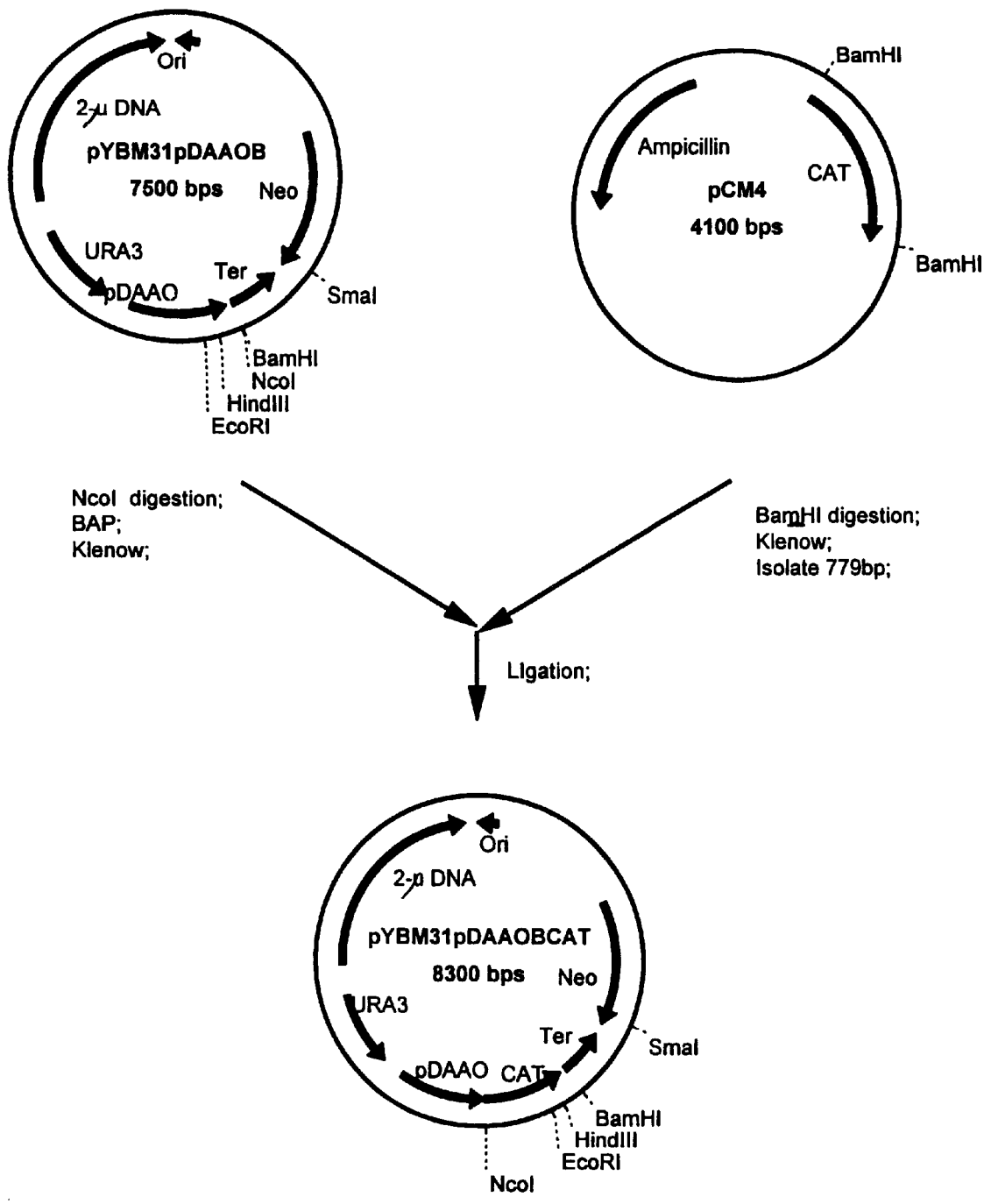
FIG. 9 Construction of pYBM31pDAAOBCAT
Figure 10:
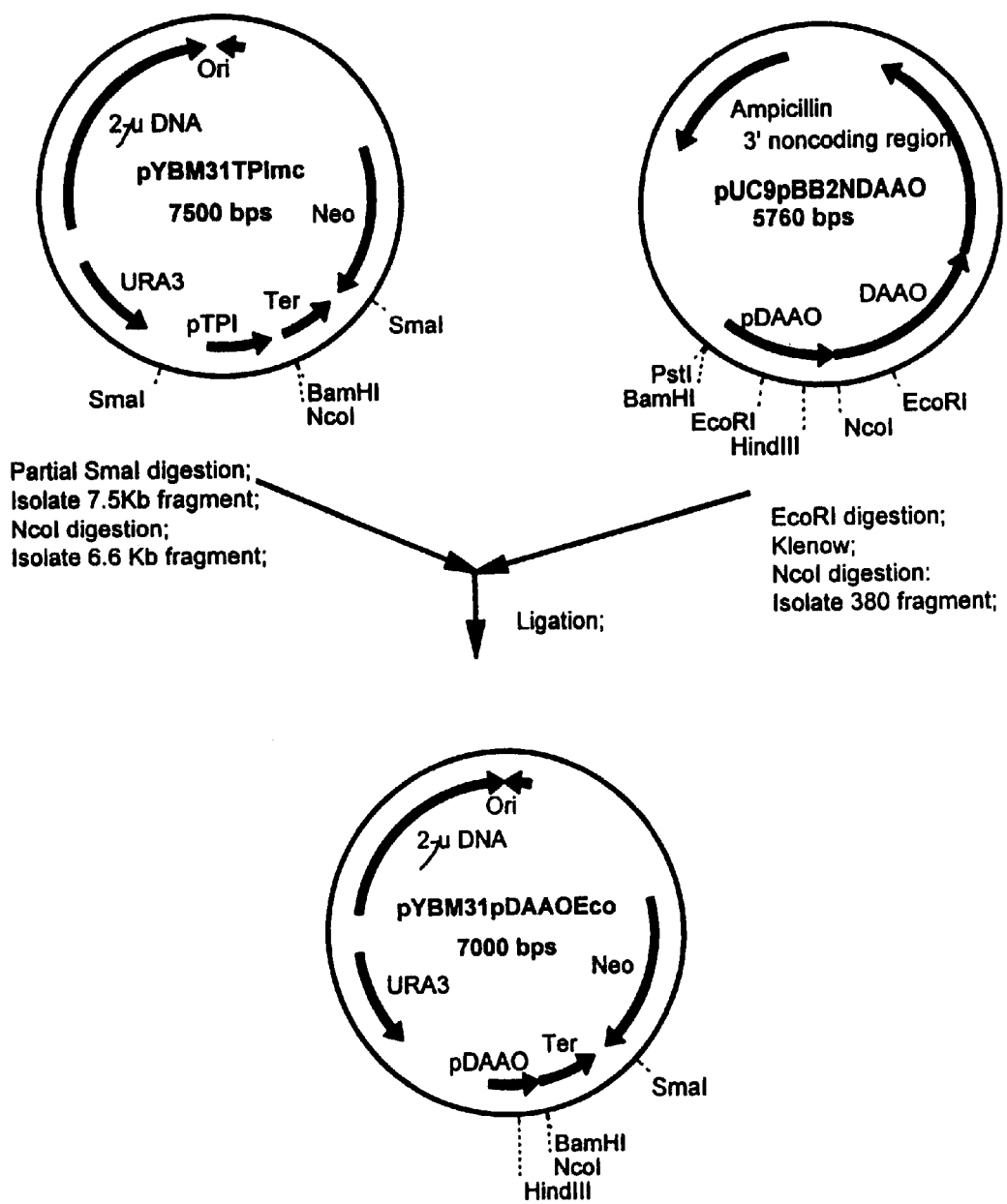
FIG. 10 Construction of pYBM31pDAAOEco
Figure 11:
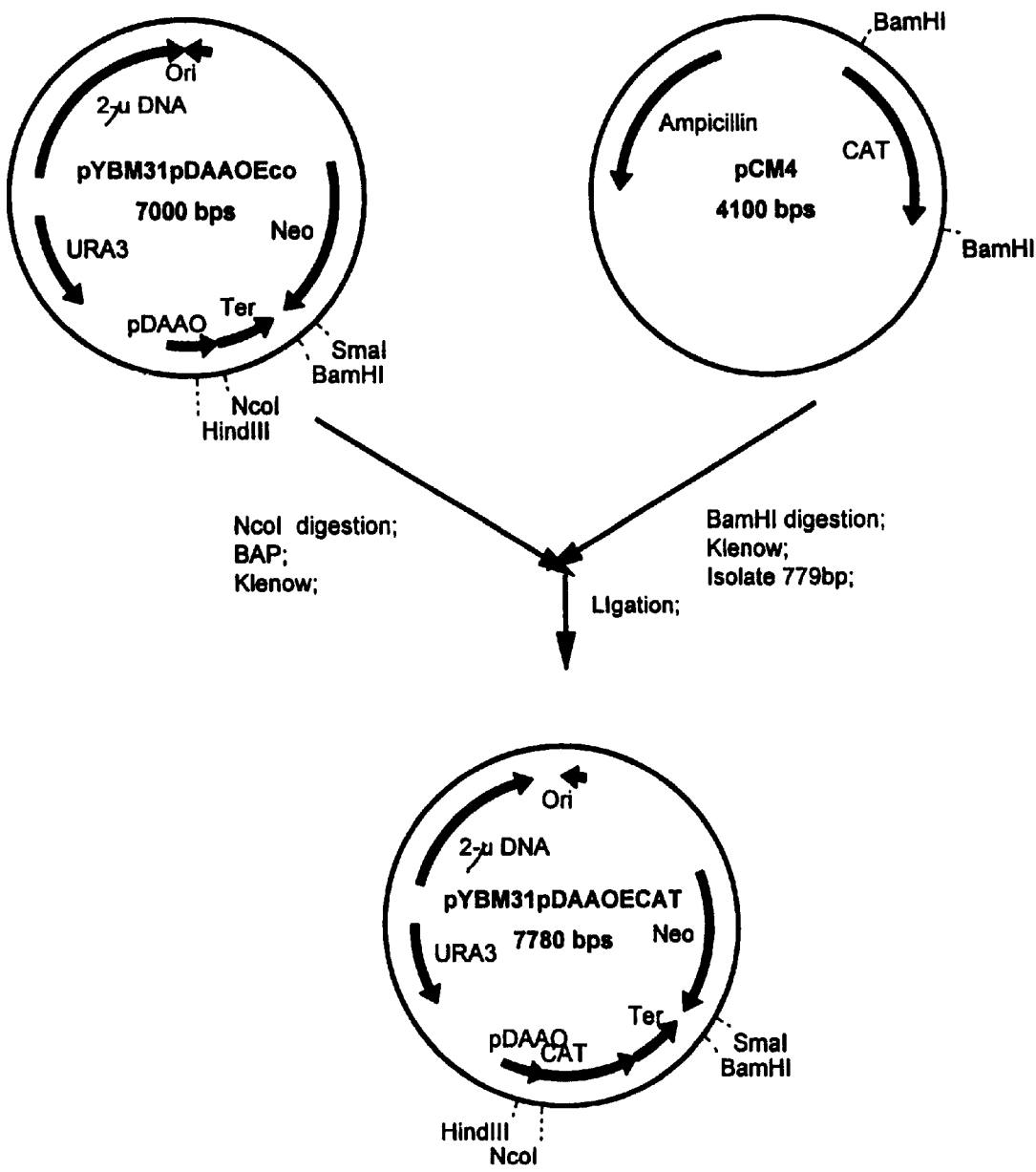
FIG. 11 Construction of pYBM31pDAAOECAT
Figure 12:
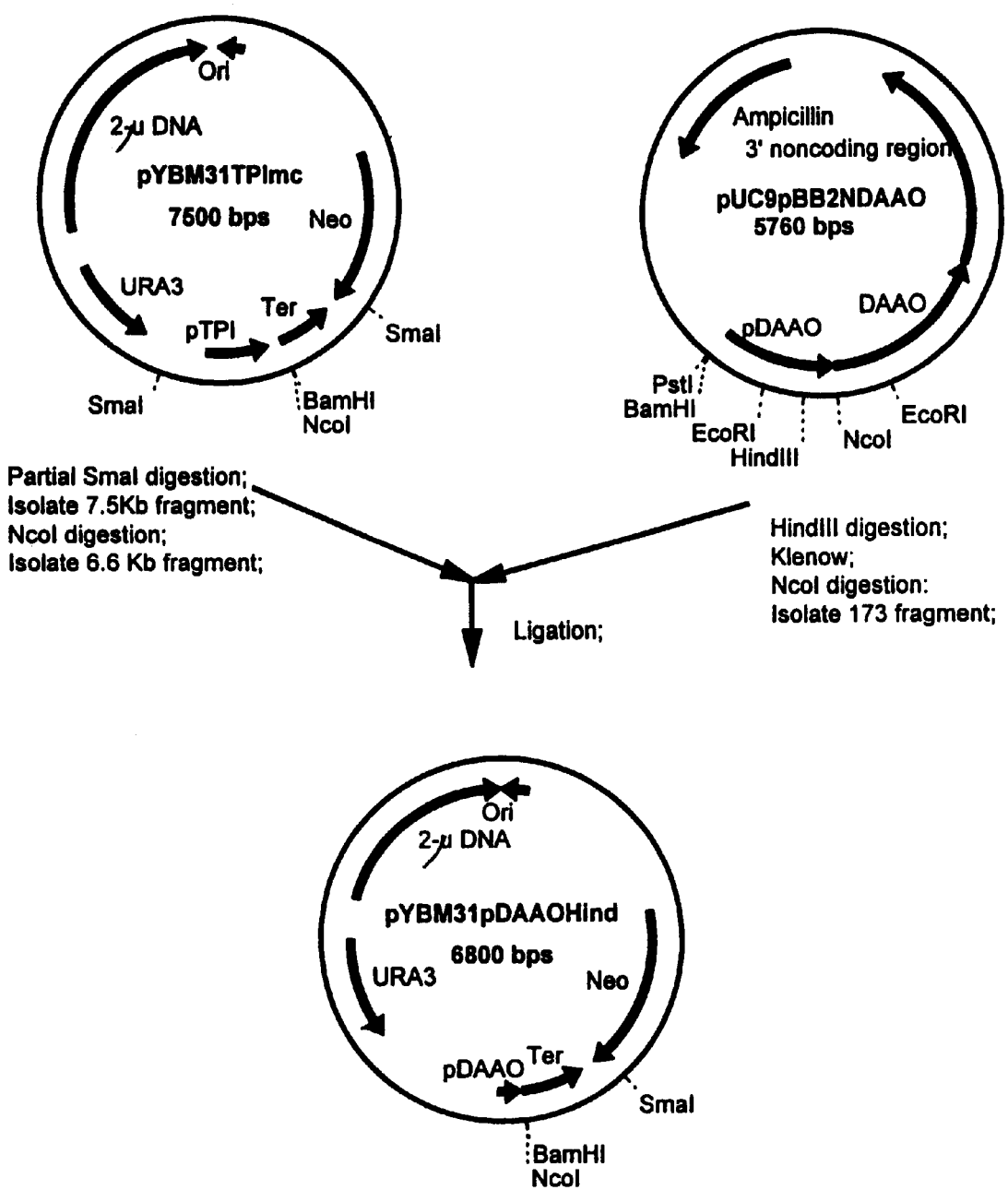
FIG. 12 Construction of pYBM31pDAAOHind
Figure 13:
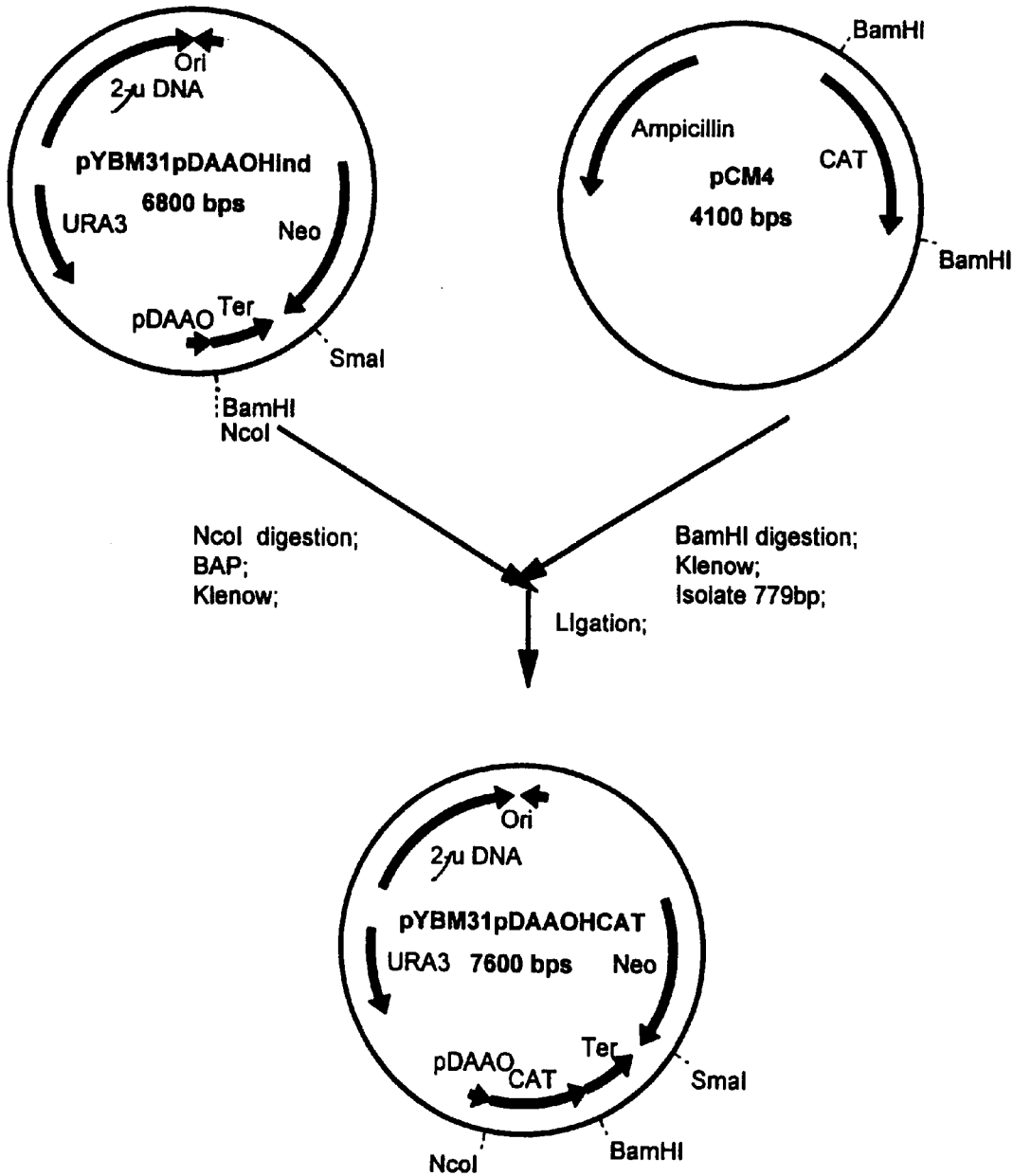
FIG. 13 Construction of pYBM31pDAAOHCAT
Figure 14:
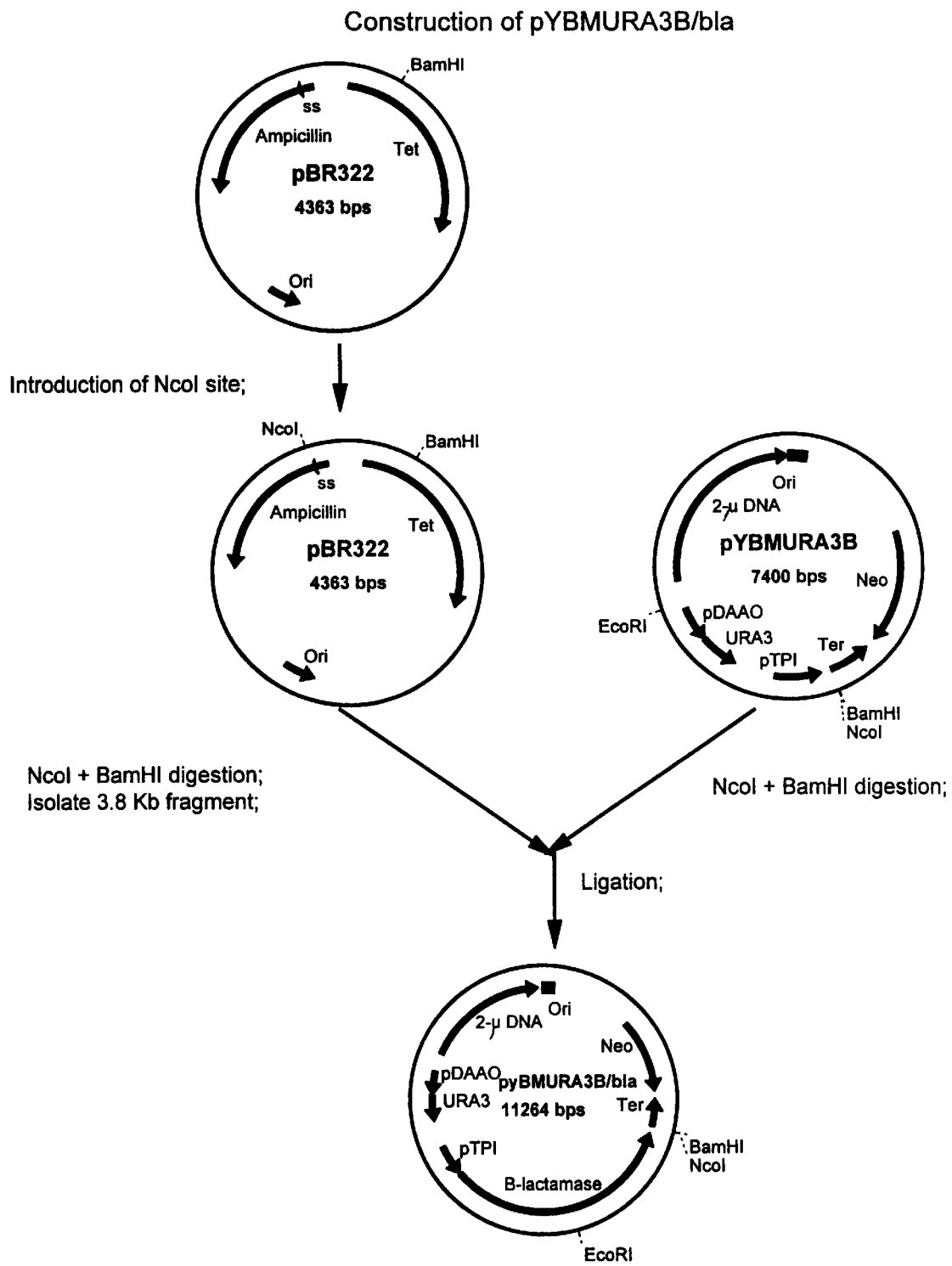
FIG. 14 Construction of pYBMURA3B/bla
Figure 15:
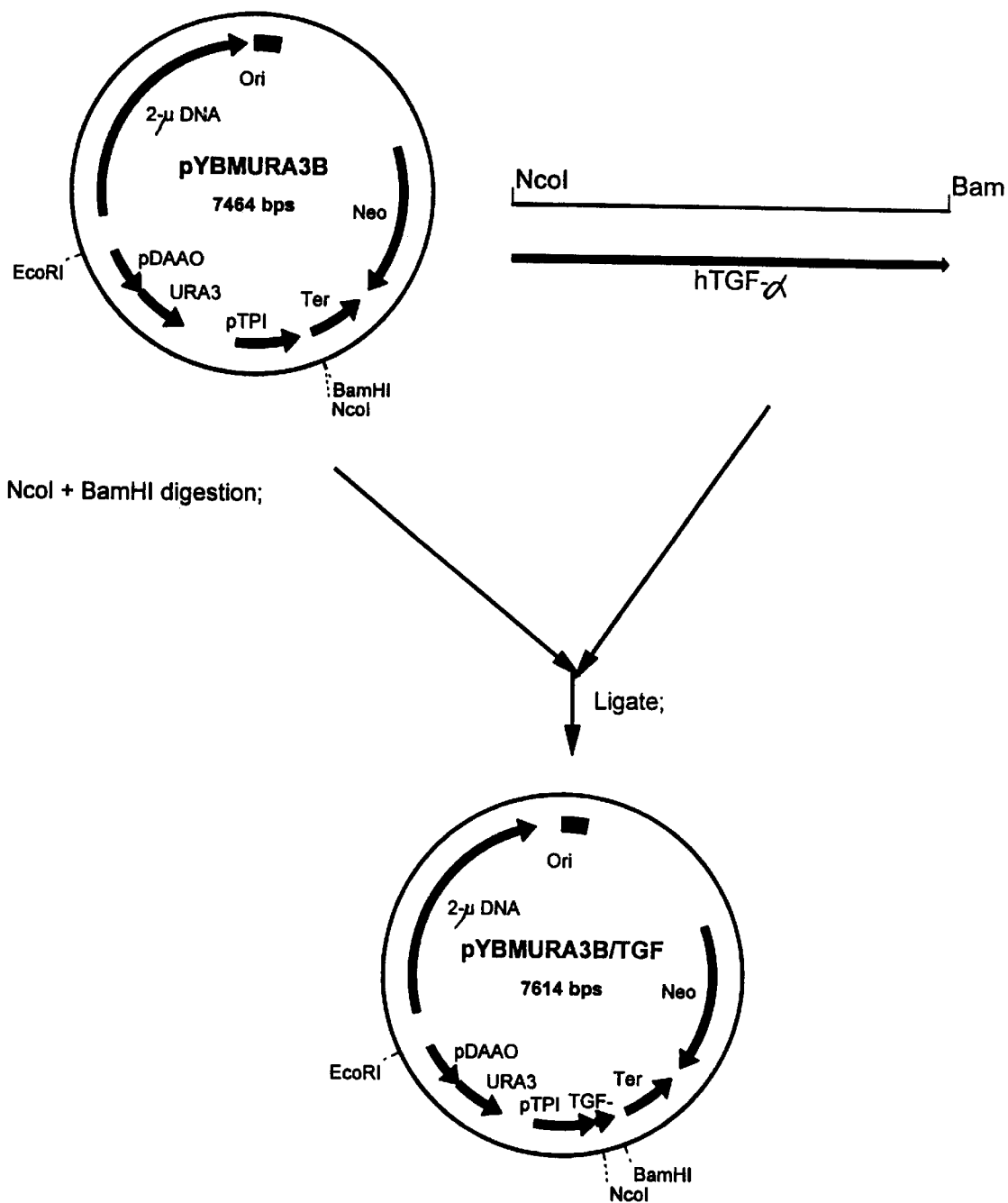
FIG. 15 Construction of pYBMURA3B/hTGF-α

| Strains and Plasmid | Relevant Characteristics | Reference |
|---|---|---|
| Escherichia coli DH5 | F-deoR recA1 endA1 hsdR17($r_K$,m) supE44-thi-1gryA96 relA1 | GlbcoBRL |
| S. cerevisiae DBY746 | α, leu2-3, leu2-112, ura3-52, his3-/-E1, trp1-289 | ATCC 44773 |
| S. cerevisiae DBY747 | a, leu2-3, leu2-112, ura3-52, his3-/-E1, trp1-289 | ATCC 44774 |
| pUC9 | $Amp^R$, 2.6 Kb | Gene 19, 259–268 (1982) |
| pUC19 | $Amp^R$, 2.6 Kb | Gene 33, 103–119 (1985) |
| pBM10 | $Neo^R$, 2.8 Kb | Canadian patent No. 335357 |
| pTPI | $Amp^R$, 4.4 KB | Journal of Molecular and Applied Genetics 1, 419–434 (1982); |
| pYEp24 | $Amp^R$, $Tet^R$, ura3, 7.77 Kb | Gene 8, 17–24 (1979) |
| pAAH5 | $Amp^R$, leu2, 12.5 Kb | Methods in Enzymology, 101, p.192 (1983) |
| pYBM31TPI | $Neo^R$, ura3, 7.55 Kb | FIG. 2 |
| pYBM31TPIm | $Neo^R$ | FIG. 2 |
| pYBM31TPImc | $Neo^R$, ura3, 7.41 Kb | FIG. 2 |
| pYBMura3B | $Neo^R$, ura3, 7.45 Kb | FIG. 3 |
| pYBMura3B/bla | $Neo^R$, ura3, 11.25 Kb | FIG. 14 |
| pYBMura3B/hTGF-α | $Neo^R$, ura3, 7.61 Kb | FIG. 15 |
| pUC9pBB2DAAOR | $Amp^R$ 5.76 kb | FIG. 7 |
| pUC9DBB2DAAOS | $Amp^R$ 5.76 kb | FIG. 7 |
| pUC9pBB2NDAAO | $Amp^R$, 5.76 kb | FIG. 8 |
| pYBM31PDAAOB | $Neo^R$, ura3, 7.5 Kb | FIG. 8 |
| pYBM31pDAAOBCAT | $Neo^R$, ura3, 8.3 Kb | FIG. 9 |
| pYBM31pDAAOEco | $Neo^R$, ura3, 7.0 Kb | FIG. 10 |
| pYBM31pDAAO | $Neo^R$, ura3, 6.8 Kb | FIG. 12 |
| pYBM31pDAAOoCAT | $Neo^R$, ura3, 7.78 Kb | FIG. 11 |
| pYBM31pDAAOCAT | $Neo^R$, ura3, 7.6 Kb | FIG. 13 |
| pEcoEcoDCO | $Amp^R$, 3.450 kb | FIG. 5 |
| pUC19pBamDAAO | $Amp^R$, 6.69 kb | FIG. 6 |

Buffer and Media

Lauria broth: 1% Difco Bacto tryptone, 0.5% Difco Bacto yeast extract, 0.5% sodium chloride Lauria agar: Luria broth supplemented with 1.5% Difco Bacto agar YPD (or YEP): 2% glucose, 2% peptone, 1% yeast extract YPD agar: YPD supplemented with 2% Difco Bacto agar SD medium: 2% dextrose, 0.7% yeast nitrogen base without amino acid, 2% Bacto agar SED: 1M sorbitol, 25 mM EDTA, pH8.0, 50 mM dithiothreitol SCE: 1M sorbitol, 0.1M sodium citrate, pH5.8, 0.01 mM EDTA SE: 1.0M sorbitol, 25 mM EDTA, pH8.0

STC: 1M sorbitol, 10 mM $CaCl_2$, 10 mM TrisHCI, pH7.5

PEG: 20% PEG4000, 10 mM $CaCl_2$, 10 mM TrisHCI, pH7.4

SOS: 50% of 2M sorbitol, 33.5% YEP, 0.65% 1M $CaCl_2$, 0.135% of 1% amino acid to be selected Top agar: 18.2% sorbitol, 2% agar, 0.67% Difco yeast nitrogen base without amino acids, 2% glucose, 0.1% adenine, 0.4% uracil, 10% of 1% amino acids as required Agar for plates: same as top agar S.O.C. medium for bacterial transformation: 2% tryptone, 0.5% yeast extract, 10 mM NaCl, 2.5 mM KCI, 10 mM $MgCl_2$, 10 mM $MgSO_4$, and 20 mM glucose

Chloramphenicol Acetyl Transferase Assay

The assay used to determine the chloramphenicol acetyl transferase activity was performed as described by C. Gorman (in DNA Cloning, Vol II, edited by D M Glove, page 156). The cells were harvested by centrifugation and resuspended in 0.25 mM Tris-HCI, pH8.0. To disrupt the cells, the cells were subjected to sonication. Cellular debris were removed by centrifugation and the supernatant saved to assay for CAT activity. The cellular extract was added to the reaction mixture containing 0.12M Tris-HCI pH7.8, [$^{14}$C] Chloramphenicol and 0.55 mM acetyl-CoA in a final volume of 150 μl. The mixture was incubated 10–30 minutes at 37° C. The chloramphenicol was extracted with ethyl acetate and the top organic phase which contain all forms of the chloramphenicol was dry down under vacuums. The pellet was resuspended in ethyl acetate and spot onto silica gel thin layer chromatography plate. The plate was subjected to ascending chromatography with a 95:5 mixture of chloroform:methanol. After air drying, the chromatography plate was exposed to X-ray film overnight.

Assay for TGF-α Activity

TGF-α activity was assayed using a kit purchased from Biomedical Technologies Inc. (Stoughton, Mass., catalog number BT-390). It is a radioassay system based on the competitive protein binding principal using membrane receptor particles as the binding protein and an [$^{125}$I] labeled EGF peptide.

Assay for β-lactamase Activity

The detection of β-lactamase activity is based on works done by O'Callaghan et al (Antimicrobial Agents and Chemotherapy 4, 283–288,1972). Cells were pelleted by centrifugation and the pellets suspended in water. The cells were disrupted by sonication and the debris were pelleted by centrifugation. The supernatant obtained is used for assays. Samples were added to 1/10 volume of 0.5 mg/ml of nitrocephin prepared in 0.5M $NaPO_4$, pH7.2. The mixture was incubated at 37° C. for 30–60 minutes and the reaction mixture was subjected to spectrophotometric reading at 482 nm.

Assay for Esterase Activity from Rhodosporidium

The detection of the esterase activity was based on the conversion of cephalosporin C to desaecetyl cephalosporin C. The cells harboring the esterase gene were harvested by centrifugation and washed once in deionized water. The cells were resuspended in deionized water at the desired density. Two hundred μl of the suspended cells were added 200 μl of cephalosporin C prepared in 0.2M $KPO_4$, pH 6.5. The cell mixture was incubated for 30 minutes at 37° C. To stop the reaction, 400 μl of $CH_3CN$ was added. Four ml of deionized water was added and 5 μl of the sample was injected onto a 5 μm C18 ODS Spherisorb column and the products eluted with a gradient of 12% methanol, 0.1% of 85% $H_3PO_4$, pH8.0.

Example 2

Transformation of E. coli

Competent DH5 was purchased from Gibco/BRL. One microliter of the ligation mixture was added to 70 µl of the competent cells in a 17 mm×100 mm Falcon tube and the mixture was incubated on ice for 30 minutes. The mixture was subjected to heat treatment 42° C. for 45 seconds and incubated on ice for 2 minutes. One ml of S.O.C. medium was added and the mixture as incubated in a gyratory incubated for 1 hour at 37° C.

Example 3

Transformation of S. Cerevisiae

An overnight culture of S. cerevisiae was prepared by adding 0.1 ml of glycerol culture to 50 ml of YEPD medium. The culture was grown at 30° C. in shaker incubator with aeration. Next morning, 5 ml of the overnight culture as diluted 1:10 in the YEPD medium and cultured for 4 hours at 30° C. with aeration. To prepare for the spheroplast, the cells were subjected to centrifugation at 3,000 rpm for 3 minutes. The precipitated cells were washed with 20 ml of sterile water. The cells were suspended in 25 ml of SE to which 1.0 ml of sterile 0.5M DTT was added.

The mixture was mixed and incubated at 30° C. with shaking for 10 to 3 minutes. The cells were pelleted by centrifugation at 3000 rpm for 3 minutes and the pellet was washed once with 200 ml SE. The washed cells were pelleted in the same manner as before and the pelleted cells were resuspended in 15 ml of SE to which 0.5 ml of 1 mg/ml zymolyase was added to the tube. The mixture was incubated at 30° C. for 20 to 30 minutes and subjected to shaking speed of 100 rpm to form spheroplasts. The spheroplasts were pelleted by centrifugation at 3,000 rpm for 3 minutes at 4° C., and washed 3 times with 30 ml of SE. The pellet was resuspended in 2.5 ml of STC. For transformation, 100 µl of the spheroplast was added to 0.5–5 µg of DNA. After incubating the mixture at room temperature for 10 minutes, 1 ml of 20% PEG was added to the tube. The mixture was incubated for 10 minutes at room temperature and subsequently centrifuged for 3 minutes at 3,000 rpm. The pellet was resuspend in 150 µl of SOS and incubated for 30 minutes at 30° C. Seven ml of top agar was added to the spheroplasts and mixed. The mixture was pour onto selection plates and incubated at 30° C. for 5 days.

Site-Specific Mutagenesis

Oligonucleotide-directed site-specific mutagenesis was performed as described by Morinaga et al (Bio/Technology 2, 636–639, 1984).

Extraction of total DNA from S. cerevisiae

Total DNA was prepared as described by F. Sherman et al (Sherman, F. et al, Laboratory Course Manual for Methods in Yeast Genetics, Cold Spring Harbor Laboratory, 1986, p125–126 or 127–128).

Preparation of Radiolabeled Probe

Radiolabeled probes were prepared using the "oligo-labelling" method as described by Feinberg and Vogelstein (Analytical Biochemistry, 132, 6–13 1983). For the detection of the DAAO promoter, the probe is an approximately 500 bp fragment obtained by the digestion of cosmid #23 containing the gene coding for D-amino acid oxidase and a small region of its promoter with restriction enzymes, EcoRI and HindIII. The 500 bp contains 283 bp of the amino terminus of the coding region of the D-amino acid oxidase gene and an approximately 230 bp of the promoter region. The probe was labeled with [$^{32}$P]dCTP using Klenow fragment. Prior to its usage in a hybridization experiment, the probe was heated at 100° C. for 5 minutes and quickly chilled on ice for 2 minutes.

For detection of the gene amplification of the plasmid containing the heterologous gene, the probe is the 1.1 Kb ura3 gene obtained by the digestion of plasmid yEp with restriction enzymes, Clal and Smal.

Southern DNA Hybridization

S. cerevisiae DNA was digested to completion with each of several different restriction enzymes and electrophoresed through a 0.7% agarose gel in TE buffer. The gels were treated by acid depurination, alkaline denaturation, neutralized and transferred to nitrocellulose membrane as described in Sambrook et al. DNA hybridization and autoradiography were carried out as described above.

DNA Sequence Analysis

The 5' upsteam region of the D-amino acid oxidase gene was determined by an automated DNA sequencer, ABI 310. The promoter sequence is SEQ.ID.NO.:1.

Example 4

Construction Of Plasmids

Construction of pYBM31

Plasmid YEP24 was subjected to partial digestion with restriction enzyme, EcoRI. The 7.76 kb linearized plasmid was isolated and subsequently digested with restriction enzyme, Bam H1. The 3.78 kb fragment was isolated and ligated to the 2.8 kb fragment generated by digestion of plasmid pBM10 with EcoRI. The resultant plasmid is named pYBM2 (6596 bp). Plasmid pYBM2 was subjected to oligonucleotide-directed site-specific mutagenesis as described by Morinaga et al to remove the restriction enzyme site, NcoI, in the neomycin phosphotransferase gene. The resultant plasmid is named pyBM3 (6596 bp). Plasmid pAAH5 (12.5 Kb) was digested with the restriction enzyme, BamHI. The 450 bp BamHI fragment containing the ADH transcription terminator was isolated and ligated to plasmid pyBM3 digested with BamHI and incubated with bacterial alkaline phosphatase to remove the 5'-phosphate. The resultant 7046 bp plasmid was named pyBM31.

Construction of pYBM31TPImc

Using oligonucleotide-directed site-directed mutagenesis, two restriction enzyme sites, NcoI and BamHI were introduced into the 3' region of the TPI promoter in plasmid pTPI. The NcoI restriction endonuclease was introduced at the junction between the end of the promoter and the initiation start site followed by the restriction endonuclease site, BamHI. The resultant plasmid was named pTPIm. The 4.4 Kb plasmid pTPIm was digested with the restriction enzyme, Avall. The 5' overhang was filled with Klenow fragment and subsequently digested with the restriction enzyme, BamHI. A 500 bp fragment containing the TPI promoter was isolated. Plasmid pyBM31 was digested with restriction enzyme, Nhe I, the 5' overhang filled in with Klenow fragment, and then subjected to partial digestion with the restriction enzyme, BamHI. The eluted 7.0 KB fragment was ligated to a 500 bp fragment of a TPI promoter obtained as described above. The resultant 7.5 Kb was named pYM31TPI. Plasmid pYM31TPI was subjected to oligonucleotide-directed site-specific mutagenesis to remove the NcoI site in the ura3 gene. The resultant plasmid was named pyBM31TPIm. To construct pyBM31TPImb (7.4 Kb), a 139 bp BamHI fragment was removed between the TPI promoter and the ADH transcription terminator sequence by digesting pyBM31TPI with BamHI. Three BamHI fragments were obtained and two fragments, the 500 bp and the 6.86 bp DNA fragments were ligated. To facilitate the cloning of a heterologous gene in the expression plasmid, one of the two BamHI restriction sites was removed, specifically, the BamHI at the 3' terminus of the ADH transcription terminator. This was accomplished by subjecting plasmid pyBM31mb to partial digestion with the restriction enzyme, BamHI. The 7.4 Kb linearized fragment was isolated and the 5' overhang filled in with Klenow fragment. The DNA was self-ligated. The resultant plasmid was named pyBM31mc.

Construction of pyBMura3B

The promoter of the gene coding for ura3 was removed from plasmid pyBM31TPImc and replaced with the DAAO promoter sequence from *Trigonopsis variabilis*. Plasmid pEcoEcoNco was digested with NcoI followed by treatment with mung bean nuclease and subsequently digested with the restriction enzyme, EcoRI. The 380 bp fragment containing the DAAO promoter was isolated. Plasmid pyBM31TPImc was digested with the restriction enzyme, BspM1 and the 5' overhang was filled in with Klenow fragment and subsequently digested with EcoRI. The 7 Kb fragment lacking the native ura3 promoter was ligated to the 370 bp fragment containing the DAAO promoter. The resultant 7.4 Kb plasmid was named pyBMURA3B.

Construction of pyBMura3Bsuc2

An expression plasmid was constructed to enable the expressed heterologous proteins to be secreted. This was accomplished by the addition of 64 bp secretion signal sequence for the gene coding for invertase downstream from the DAAO promoter on plasmid pyBMURA3B. The secretion signal was synthesized using ABI gene synthesizer.

Construction of pEcoEco

Cosmid #6 containing the promoter region of the D-amino oxidase and the genomic sequence of the D-amino acid oxidase was digested with EcoR1. A DNA fragment with approximately 670 bp was excised and cloned into pUC9 digested with EcoR1 and the 5'-phosphate removed with alkaline phosphatase. The resultant is named pEcoEco. This 670 bp fragment contains the promoter sequence of D-amino acid oxidase. The resultant plasmid was named pEcoEco.

Plasmid pEcoEco is subjected to mutagenesis as described by Morinaga et al (Bio/Technology 2, 636–639, 1984). A NcoI restriction enzyme site was introduced into pEcoEco at the 3' region of the promoter or at the translation initiation site of the D-amino acid oxidase gene. The resultant plasmid is named pEcoEcoNco.

Construction of pUC19pBamDAAO

Cosmid #6 containing the gene coding for D-amino acid oxidase and its promoter from *Trigonopsis variabilis* was digested with the restriction enzyme, BamHI. Southern hybridization was performed to determined the DNA bands which contain the promoter sequence. The area corresponding to the migration position of 4 Kb hybridized to the probe. As that area contains 3 DNA bands migrating closely to each other, all three bands were excised, the DNA electroeluted, and subsequently ligated to pUC19 digested with the restriction enzyme, BamHI and treated with bacterial alkaline phosphatase to remove the 5'-phosphate. The ligation mixture was introduced into *E. coli* using bacterial transformation technique described above. To obtain an *E. coli* containing the promoter sequence, the *E. coli* transformants obtained were subjected to colony hybridization. Colonies which hybridized to the probe were expanded and verified to contain the promoter sequence by Southern hybridization. One of the transformants containing the promoter sequence is named pUC19pBamDAAO. This 40 kb BamHI fragment contains the entire coding region of the D-amino acid oxidase (1068) bp, approximately 1330 bp of 3' non-coding region and 1600 bp of 5' upstream sequences which includes the D-amino acid oxidase promoter (SEQ.ID.NO.:1).

Construction of pUC9pBB2DAAO

To reduce the length of the promoter, plasmid pUC19pBamDAAO was digested with BamHI and BglII. The 3.1 kb fragment was eluted and ligated to BamHI digested pUC9(ER) and the 5'-phosphate group removed by treatment with bacterial alkaline phosphatase. Plasmid pUC9 (ER) ws constructed by digesting pUC19 with restriction enzymes EcoRI, the 5'-overhang filled in with klenow fragment and self-ligated. Both orientations of the inserted DNA were obtained. Depending on the orientation of the insert, the resultant plasmids were named either pUC9pBB2DAAOR (#4) or pUC9pBB2DAAOS (#3).

Construction of pYBM3pDAAOB

Plasmid pUC9pBB2DAAOS was digested with restriction enzyme, EcoRI, and the 5-phosphate group removed by treatment with bacterial alkaline phosphatase. The DNA was separated on the agarose gel and the 5.06 kb fragment was electroeluted and ligated to the 700 bp fragment obtained by the digestion of plasmid pEcoEcoNco with EcoRI. The resultant plasmid is named pUC19pBB2NDAAO. Plasmid pYBM31TPImc was subjected to partial digestion with the restriction enzyme, SmaI. The linearized 7.5 Kb fragment was electroeluted and subsequently digested with NcoI. The DNA fragments were separated on the agarose gel and the 6.64 Kb fragment isolated by electroelution. Plasmid pUC9pBB2NDAAO was digested with restriction enzyme, PstI, treated with T4 DNA polymerase to remove 3' overhang, and then digested with NcoI. The DNA fragments were separated on the agarose gel. The 850 bp fragments was electroeluted and ligated to the 6.64 bp fragment mentioned above. The resultant plasmid was named pyBM31pDAAOB.

Construction of pyBM3pDAAOBCAT

Plasmid pyBM31pDAAOB was digested with NcoI, the 5-phosphate removed by treatment with bacterial alkaline phosphatase, and the 5' overhang filled in with Klenow fragment. This fragment was ligated to the 779 bp CAT fragment generated by digestion of pCM4 (Pharmacia) with BamHI followed by Klenow treatment to fill in the 5' overhang. The resultant 8.3 Kb plasmid was named pyBM31pDAAOBCAT.

Construction of pyBM31DAAOEco

Plasmid pyBM31TPImc was subjected to partial digestion with restriction enzymes, SmaI. The linearized fragment was isolated by agarose gel fractionation followed by electroelution of the 7.5 kb which was subsequently digested with NcoI and the 6.6 Kb fragment was isolated. Plasmid pUC19pBB2NDAAO was digested with restriction enzyme, EcoRI, the 5'-overhang filled in with Klenow fragment and subsequently digested with the restriction enzyme, NcoI. The 380 bp fragment was isolated and ligated to the 6.6 Kb fragment. The resultant plasmid is named pYBM31DAAOEco.

Construction of pyBM31DAAOHind

Plasmid pyBM31TPImc was digested with restriction enzymes, SmaI and NcoI and the 6.6 Kb fragment was isolated. Plasmid pUC19pBB2NDAAO was digested with restriction enzyme, HindIII, the 5'-overhang filled in with Klenow fragment and subsequently digested with the restriction enzyme, NcoI. The 173 bp fragment was isolated and ligated to the 6.6 Kb fragment. The resultant 6.76 Kb plasmid is named pyBM31DAAOHind.

Construction of p pyBM31DAAOECAT

Plasmid pYM31DAAOEco was digested with the restriction enzyme, NcoI followed by treatment with bacterial alkaline phosphatase to remove the 5' phosphate. The 5' overhang was filled in using the large fragment of DNA polymerase (Klenow). The gene coding for chloramphenicol acetyltransferase (CAT) was obtained by the digestion of plasmid pCM4 (Pharmacia) with the restriction enzyme, BamHI. The 5'-overhang was filled in by the Klenow and the 779 bp fragment containing the CAT gene was isolated and ligated to pyBM31DAAOEco. The resultant 7.78 Kb plasmid is named pyBM31DAAOECAT.

Construction of pyBM31DAAOHCAT

Plasmid pYM31DAAOHindIII was digested with the restriction enzyme, NcoI followed by treatment with bacterial alkaline phosphatase to remove the 5' phosphate. The 5' overhang was filled in using Klenow fragment. The gene coding for CAT was obtained by the digestion of plasmid pCM4 with the restriction enzyme, BamHI. The 5'-overhang was filled in by the Klenow fragment and the 779 bp fragment containing the CAT gene was isolated and ligated to pyBM31DAAOHind. The resultant 7.54 Kb plasmid is named pyBM31DAAOHindCAT.

Construction of pyBMura3B/bla

To remove the secretion signal from the β-lactamase gene in plasmid pBR322, a NcoI restriction enzyme was introduced at the junction of the secretion signal sequence and the mature gene by oligonucleotide-directed mutagenesis. The 3.8 Kb β-lactamase gene minus the secretion signal was isolated by digestion with restriction enzymes, NcoI and BamHI, and subcloned into pYBMura3B, digested with restriction enzymes, NcoI and BamHI. The resultant plasmid was named pYBMURA3B/bla.

Construction of pYBMura3B/hTGF-α

The gene coding for human TGF-α was synthesized chemically using the state of art technology. Restriction enzyme sites, NcoI and Bam HI were added at the 5' and 3' ends respectively to facilitate the subcloning of this gene into pYBM31URA3B digested with restriction enzymes, NcoI and BamHI. The resultant plasmid was named pYBM31URA3B/hTGF-α.

Construction of pYBMura3Bsuc/hTGF-α

The construction of pYBMURA3Bsuc/hTGF-α was similar to the construction of pYBMURA3B/hTGF. The TGF-α gene was subcloned into pYBMURA3Bsuc digested with restriction enzymes, NcoI and BamHI.

Example 5

D-amino Oxidase Promoter Sequence From *Trigonopsis variabilis* (SEQ.ID.NO.:1)

AAACAGCCCATGATTAGACTTTCTGCCATGACAGCACTATAACGTGATAT

GATAAGTAAG

GTTTTGTTGCCCGCTGACGGCCAACGGCTGACGGCCAANTTGATGATTCTA

CCACAAAAA

ATCATACGGAGAAGTCAACGAAAAGTCCCTTAGTTTGGAATTCCAGACAT

GGCAGAATTT

AACGGCCACTACAGTTGGCCGTTCGTAAACGAGACAAGTGACTCATGGCA

GCACCGTCTC

AGTCCACCGGTCTAAAGCACTTGGTGCCAGATGAATTTGGAAACTGTCAC

CTTATAGAAT

TACTTTTGGATAGTTTTTGTAAGGCTGGAGACTTGTAAGCCTGACTCAGTT

GACTCATCG

GCGAAAGCTTCCTATCTTGGAGCTAAGATCGCCTGATCGTTTTGCCCTACT

TATCTTGGT

TGCATGAGTTGGCCGGTCAGAGCCGCATTCTAGCCAAAGGGTTATAGCGT

TACACTCTTG

ATAGGCAAATCCGTGCTCGGATTATATATAAGGCAAAAGTCGATTCAACG

GATCAATAAA

A

Example 6

Increased expression of β-lactamase

The gene coding β-lactamase was inserted in the plasmid pYBMura3B. This plasmid was introduced into yeast DBY746. Intracellular levels of β-lactamase were assayed in DBY746 transformants spectrophotometrically by the hydrolysis of the chromogenic substrate nitrocefin (O'Callaghan et al. 1972 Antimicrobial Agents and Chemotherapy 1:283). Two independent isolate of the transformants was subjected to assay for β-lactamase activity.

TABLE 2

| DBY 746 Transformants | β-lactamase Activity $OD_{482}$/min/ml at 37° C. |
| --- | --- |
| pYM31TPImc (control) | 38 |
| pYBMura3B A | 105 |
| pYBMura3B B | 103 |

Example 7

Expression of TGF-α

The gene coding for TGF-α was cloned into plasmid pyBMura3B (for intracellular expression) and pYBMura3Bsuc2 (for extracellular expression) and transformed into DBY746. The cells were pelleted by centrifugation and the medium was measured for the presence of human TGF-α. For the measurement of the intracellular human TGF-α, the pelleted cells were resuspended and raptured as described. The levels of intracellular and extracellular human TGF-α were assayed using an EGF radioassay kit (Biomedical Technologies, Inc.)

TABLE 3

| DBY746 Transformants | TGF-α (ng/ml) |
|---|---|
| pYBM31TPI (control) | 159 |
| pYBMura3B | 272 |
| PYBMura3BSuc2* | 2,000 |

*secretion plasmid

Example 8

Expression of *Rhodosporidium esterase*

The cDNA coding for *Rhodosporidium esterase* was cloned into plasmid pyBMura3B and transformed into DBY746. The cells were washed and subjected to assay for esterase activity.

| DBY746 | Esterase Activity (iu/ml) |
|---|---|
| pYBMura3B | 0.2 |

What is claimed is:

1. An isolated nucleic acid molecule encoding a D-amino acid oxidase promoter from *T. variabilis*, said isolated nucleic molecule consisting of a sequence as shown in SEQ.ID.NO:1 or a fragment thereof which functions as a promoter.

2. An isolated nucleic acid molecule consisting of a sequence complementary to the sequence of claim 1.

3. An isolated nucleic acid molecule consisting of a sequence capable of hybridizing under stringent conditions to the isolated nucleic acid of claim 2, with the proviso that the D-amino acid oxidase coding region does not comprise any portion of said isolated nucleic acid molecule.

4. An expression vector comprising the nucleic acid sequence of claim 1 or claim 3.

5. The expression vector of claim 4 which is a plasmid.

6. The expression vector of claim 5 further comprising a selectable marker sequence.

7. The expression vector of claim 6 further comprising an ARS sequence.

8. The expression vector of claim 7 further comprising an origin of replication, a strong promoter, a selectable marker, and a transcription termination sequence.

9. A plasmid selected from the group consisting of pYBM31TPI, pYBM31TPIm, pYBM31TPImc, pYBM31TPImcSuc2, pYMB31ura3Bsuc2, pYBMura3B, pYBMura3B/bla, pYBMura3B/hTGF-α, PYBMura3Bsuc2/hTGF-α, pYBM31DDAAOB, pYBM31DDAAOBCAT, pYBM31DAAOEco, pYBM31DAAHind, pYBM31DAAOECAT, pYBMura3Bsuc2, and pYBM31DAAHCAT.

10. A plasmid selected from the group consisting of pYBM31DDAAHCAT, pYBM31DAAOECA, pYMB31ura3Bsuc2, pYBMura3Bsuc2, pYBM31DAAHind, pYBM31DAAOEco, pYBMura3B and pYBM31PDAAOBCAT.

11. The plasmid of claim 10 which is pYBM31DAAHCAT.

12. The plasmid of claim 10 which is pYBM31DAAOECAT.

13. The plasmid of claim 10 which is pYBM31DAAHind.

14. The plasmid of claim 10 which is pYBM31DAAOEco.

SEQUENCE LISTING

<160> NUMBER OF SEQ ID NOS: 1

<210> SEQ ID NO 1
<211> LENGTH: 541
<212> TYPE: DNA
<213> ORGANISM: Trigonopsis variabilis

<400> SEQUENCE: 1

```
aaacagccca tgattagact ttctgccatg acagcactat aacgtgatat gataagtaag      60
gttttgttgc ccgctgacgg ccaacggctg acggccaaat tgatgattct accacaaaaa     120
atcatacgga gaagtcaacg aaaagtccct tagtttggaa ttccagacat ggcagaattt     180
aacggccact acagttggcc gttcgtaaac gagacaagtg actcatggca gcaccgtctc     240
agtccaccgg tctaaagcac ttggtgccag atgaatttgg aaactgtcac cttatagaat     300
tacttttgga tagtttttgt aaggctggag acttgtaagc ctgactcagt tgactcatcg     360
gcgaaagctt cctatcttgg agctaagatc gcctgatcgt tttgccctac ttatcttggt     420
tgcatgagtt ggccggtcag agccgcattc tagccaaagg gttatagcgt tacactcttg     480
ataggcaaat ccgtgctcgg attatatata aggcaaaagt cgattcaacg gatcaataaa     540
a                                                                     541
```

15. The plasmid of claim 10 which is pYBM31PDAAOBCAT.

16. The plasmid of claim 10 which is pYBMura3Bsuc2.

17. The plasmid of claim 10 which is pYBMura3B.

18. A host cell containing the expression vector of claim 4.

19. A host cell containing the expression vector of claim 5.

20. A host cell containing the expression vector of claim 6.

21. A host cell containing the expression vector of claim 7.

22. A host cell containing the expression vector of claim 8.

23. A host cell containing the expression vector of claim 9.

24. A host cell containing the expression vector of claim 10.

25. A host cell containing the expression vector of claim 16.

26. A host cell containing the expression vector of claim 17.

27. The host cell of claim 18 which is eukaryotic.

28. The host cell of claim 27 which is fungal.

29. The host cell of claim 28 which is a member of the genus Saccharomyces.

30. *Saccharomyces cerevisiae* ATCC 44773 containing plasmid pYBMura3B.

31. *Saccharomyces cerevisiae* ATCC 44774 containing plasmid pYBMura3Bsuc2.

32. *Escherichia coli* ATCC 98469.

33. *Escherichia coli* ATCC 98470.

34. A method for producing a polypeptide comprising culturing the host cell of claim 18 in a suitable culture medium under conditions resulting in expression of the polypeptide.

* * * * *